(12) United States Patent
Yang et al.

(10) Patent No.: US 12,195,497 B2
(45) Date of Patent: Jan. 14, 2025

(54) METHOD FOR SEPARATING AND PURIFYING RECOMBINANT HUMAN FIBRONECTIN FROM GENETICALLY ENGINEERED RICE SEED

(71) Applicant: WUHAN HEALTHGEN BIOTECHNOLOGY CORP, Wuhan (CN)

(72) Inventors: Daichang Yang, Wuhan (CN); Quan Zhan, Wuhan (CN)

(73) Assignee: WUHAN HEALTHGEN BIOTECHNOLOGY CORP, Wuhan (CN)

( * ) Notice: Subject to any disclaimer, the term of this patent is extended or adjusted under 35 U.S.C. 154(b) by 750 days.

(21) Appl. No.: 17/312,875

(22) PCT Filed: Dec. 6, 2019

(86) PCT No.: PCT/CN2019/123762
§ 371 (c)(1),
(2) Date: Jun. 10, 2021

(87) PCT Pub. No.: WO2020/119609
PCT Pub. Date: Jun. 18, 2020

(65) Prior Publication Data
US 2022/0056071 A1    Feb. 24, 2022

(30) Foreign Application Priority Data
Dec. 10, 2018 (CN) .................. 201811505129.2

(51) Int. Cl.
| | |
|---|---|
| *C07K 1/18* | (2006.01) |
| *B01D 15/20* | (2006.01) |
| *B01D 15/36* | (2006.01) |
| *B01D 15/42* | (2006.01) |
| *C07K 1/14* | (2006.01) |
| *C07K 1/34* | (2006.01) |
| *C07K 1/36* | (2006.01) |
| *C07K 14/78* | (2006.01) |
| *C12N 15/82* | (2006.01) |

(52) U.S. Cl.
CPC .............. *C07K 1/18* (2013.01); *B01D 15/203* (2013.01); *B01D 15/362* (2013.01); *B01D 15/363* (2013.01); *B01D 15/426* (2013.01); *C07K 1/145* (2013.01); *C07K 1/34* (2013.01); *C07K 1/36* (2013.01); *C07K 14/78* (2013.01); *C12N 15/8257* (2013.01)

(58) Field of Classification Search
CPC . C07K 14/78; C07K 1/36; C07K 1/34; C07K 1/145; C07K 1/18
See application file for complete search history.

(56) References Cited

U.S. PATENT DOCUMENTS

| | | | |
|---|---|---|---|
| 9,951,100 B2 | 4/2018 | Yang et al. | |
| 10,730,926 B2 | 8/2020 | Yang et al. | |
| 2008/0010697 A1* | 1/2008 | Yang .................. | C12N 15/8216 800/278 |
| 2012/0165509 A1* | 6/2012 | Yang .................. | B01J 20/3285 530/364 |

FOREIGN PATENT DOCUMENTS

| | | |
|---|---|---|
| CN | 102532254 A | 7/2012 |
| CN | 102994514 A | 3/2013 |
| CN | 103589706 A | 2/2014 |
| CN | 103880947 A | 6/2014 |
| CN | 104109204 A | 10/2014 |

OTHER PUBLICATIONS

Kuo YC, Tan CC, Ku JT, Hsu WC, Su SC, Lu CA, Huang LF. Improving pharmaceutical protein production in *Oryza sativa*. Int J Mol Sci. Apr. 24, 2013;14(5):8719-39. doi: 10.3390/ijms14058719. PMID: 23615467; PMCID: PMC3676753. (Year: 2013).*
Millipore; Recombinant Fibronectin; https://www.emdmillipore.com/US/en/product/Human-Plasma-Fibronectin-Purified-Protein, MM_NF-FC010?ReferrerURL=https%3A%2F%2Fwww.google.com%2F (Year: 2018).*
Good's Buffers; Wikipedia; https://web.archive.org/web/20180406113127/http://en.wikipedia.org:80/wiki/Good's_buffers (Year: 2018 ).*
Okumura, Masaki, et al. "Acceleration of disulfide-coupled protein folding using glutathione derivatives." The FEBS journal 278.7 (2011): 1137-1144. (Year: 2011).*

(Continued)

*Primary Examiner* — Suzanne M Noakes
(74) *Attorney, Agent, or Firm* — Gregory P. Einhorn; Greer, Burns & Crain, Ltd.

(57) ABSTRACT

Disclosed is a chromatographic method for separating and purifying a recombinant human fibronectin from a genetically engineered rice seed that expresses the human fibronectin. In the method, the genetically engineered rice seed is milled, mixed with an extraction buffer, and then filtered to obtain a crude extract comprising the recombinant human fibronectin; the crude extract comprising the recombinant human fibronectin is subjected to cation exchange chromatography, so as to perform primary separation and purification, thereby obtaining a primary product comprising the recombinant human fibronectin; and the primary product is subjected to anion exchange chromatography so as to perform final separation and purification to obtain the recombinant human fibronectin as a target substance. The method is low cost and easily utilized on an industrial scale. The obtained OsrhFn target substance has a SEC-HPLC purity greater than 95% with excellent bioactivity.

2 Claims, 13 Drawing Sheets

Specification includes a Sequence Listing.

(56) References Cited

OTHER PUBLICATIONS

GE Healthcare; www.fredhutch.org/content/dam/stripe/hahn/methods/biochem/Ion_Exchange_Chromatography_Handbook.pdf (Year: 2016).*

Shoji. Y. et al. "A Fibronectin-binding Protein from Rice Bran with Cell Adhesion Activity for Animal Tumor Cells." Bioscience, Biotechnology, and Biochemistry., vol. 65, No. (5), Dec. 31, 2001 (Dec. 31, 2001), pp. 1181-1186.

Japanese Office Action dated Nov. 30, 2020 for Japanese Patent Application No. 2021-533137.

Japanese Office Action dated May 23, 2020 for Japanese Patent Application No. 2021-533137.

Korean Office Action dated Jun. 24, 2021 for Korean Application No. 10-2021-7019636.

\* cited by examiner

| Peak # | Retention time [min] | Signal | Type | Peak area mAU *s | Peak height [mAU] | Peak area % |
|---|---|---|---|---|---|---|
| 1 | 17.362 | 1 | MF R | 238.76923 | 6.39854 | 3.4396 |
| 2 | 19.089 | 1 | FM R | 6506.78467 | 79.80427 | 93.7346 |
| 3 | 27.412 | 1 | MF R | 172.40854 | 8.85444e-1 | 2.4837 |
| 4 | 30.401 | 1 | FM R | 23.74477 | 2.34574e-1 | 0.3421 |
| Total: | | | | 6941.70720 | 87.32282 | |

SEQUENCE LISTING

<160> NUMBER OF SEQ ID NOS: 3

<210> SEQ ID NO 1
<211> LENGTH: 5637
<212> TYPE: DNA
<213> ORGANISM: Artificial
<220> FEATURE:
<223> OTHER INFORMATION: Codon-optimized human FN genes

<400> SEQUENCE: 1

| | | | | | |
|---|---|---|---|---|---|
| atgcaggccc | agcagatggt | gcagccgcag | agcccggtgg | ccgtgagcca | gagcaagccg          60 |
| ggctgctacg | acaacggcaa | gcactaccag | atcaaccagc | agtgggagcg | cacctacctc         120 |
| ggcaacgccc | tcgtgtgcac | ctgctacggc | ggcagccgcg | gcttcaactg | cgagagcaag         180 |
| ccggaggccc | aggagacctg | cttcgacaag | tacaccggca | cacctaccg | cgtgggcgac         240 |
| acctacgagc | gcccgaagga | cagcatgatc | tgggactgca | cctgcatcgg | cgccggccgc         300 |
| ggccgcatca | gctgcaccat | cgccaaccgc | tgccacgagg | gcggccagag | ctacaagatc         360 |
| ggcgacacct | ggcgccgccc | gcacgagacc | ggcggctaca | tgctcgaatg | cgtgtgcctc         420 |
| ggcaacggca | agggcgagtg | gacctgcaag | ccgatcgccg | agaagtgctt | cgaccacgcc         480 |
| gccggcacca | gctacgtggt | gggcgagacc | tgggagaagc | cgtaccaggg | ctggatgatg         540 |
| gtggactgca | cctgcctcgg | cgagggcagc | ggccgcatca | cctgcaccag | ccgcaaccgc         600 |
| tgcaacgacc | aggacacccg | caccagctac | cgcatcggcg | acacctggag | caagaaggac         660 |
| aaccgcggca | acctcctcca | gtgcatctgc | accggcaacg | gccgcggcga | gtggaagtgc         720 |
| gagcgccaca | ccagcgtgca | gaccaccagc | agcggcagcg | gcccgttcac | cgacgtgcgc         780 |
| gccgccgtgt | accagccgca | gccgcacccc | gagccgccgc | cgtacggcca | ctgcgtgacc         840 |
| gacagcggcg | tggtgtacag | cgtgggcatg | cagtggctca | agacccaggg | caacaagcag         900 |
| atgctctgca | cctgcctcgg | caacggcgtg | agctgccagg | agaccgccgt | gacccagacc         960 |
| tacggcggca | acagcaacgg | cgagccgtgc | gtgctcccgt | tcacctacaa | cggccgcacc        1020 |
| ttctacagct | gcaccaccga | gggccgccag | gacggccacc | tctggtgcag | caccaccagc        1080 |
| aactacgagc | aggaccagaa | gtacagcttc | tgcaccgacc | acaccgtgct | cgtgcagacc        1140 |
| cgcggcggca | acagcaacgg | cgccctctgc | cacttcccgt | tcctctacaa | caaccacaac        1200 |
| tacaccgact | gcaccagcga | gggccgccgc | gacaacatga | agtggtgcgg | caccacccag        1260 |
| aactacgacg | ccgaccagaa | gttcggcttc | tgcccgatgg | ccgccacgac | ggagatctgc        1320 |
| accaccaacg | agggcgtgat | gtaccgcatc | ggcgaccagt | gggacaagca | gcacgacatg        1380 |
| ggccacatga | tgcgctgcac | ctgcgtgggc | aacggccgcg | gcgagtggac | ctgcatcgcc        1440 |
| tacagccagc | tccgcgacca | gtgcatcgtg | gacgacatca | cctacaacgt | gaacgacacc        1500 |
| ttccacaagc | gccacgagga | gggccacatg | ctcaactgca | cctgcttcgg | ccagggccgc        1560 |
| ggccgctgga | agtgcgaccc | ggtggaccag | tgccaggaca | gcgagaccgg | cacctttctac        1620 |
| cagatcggcg | acagctggga | gaagtacgtg | cacggcgtgc | gctaccagtg | ctactgctac        1680 |
| ggccgcggca | tcgcgagtg | gcactgccag | ccgctccaga | cctacccgag | cagcagcggc        1740 |
| ccggtggagg | tgttcatcac | cgagaccccg | agccagccga | acagccaccc | gatccagtgg        1800 |
| aacgccccgc | agccgagcca | catcagcaag | tacatcctcc | gctggcgccc | gaagaacagc        1860 |
| gtgggccgct | ggaaggaggc | caccatcccg | ggccacctca | cagctacac | catcaagggc        1920 |
| ctcaagccgg | gcgtggtgta | cgagggccag | ctcatcagca | tccagcagta | cggccaccag        1980 |
| gaggtgaccc | gcttcgactt | caccaccacc | agcaccagca | cccggtgac | cagcaacacc        2040 |

```
gtgaccggcg agaccacccc gttcagcccg ctcgtggcca ccagcgagag cgtgaccgag    2100
atcaccgcca gcagcttcgt ggtgagctgg gtgagcgcca gcgacaccgt gagcggcttc    2160
cgcgtggagt acgagctcag cgaggagggc gacgagccgc agtacctcga cctcccgagc    2220
accgccacca gcgtgaacat cccggacctc ctcccgggcc gcaagtacat cgtgaacgtg    2280
taccagatca gcgaggacgg cgagcagagc ctcatcctca gcaccagcca gaccaccgcc    2340
ccggacgccc gccggacac caccgtggac caggtggacg acaccagcat cgtggtgcgc    2400
tggagccgcc cgcaggcccc gatcaccggc taccgcatcg tgtacagccc gagcgtggag    2460
ggcagcagca ccgagctcaa cctcccggag accgccaaca gcgtgaccct cagcgacctc    2520
cagccgggcg tgcagtacaa catcaccatc tacgccgtgg aggagaacca ggagagcacc    2580
ccggtggtga tccagcagga gaccaccggc accccgcgca gcgacaccgt gccgagcccg    2640
cgcgacctcc agttcgtgga ggtgaccgac gtgaaggtga ccatcatgtg gaccccgccg    2700
gagagcgccg tgaccggcta ccgcgtggac gtgatcccgg tgaacctccc gggcgagcac    2760
ggccagcgcc tcccgatcag ccgcaacacc ttcgccgagg tgaccggcct cagcccgggc    2820
gtgacctact acttcaaggt gttcgccgtg agccacggcc gcgagagcaa gccgctcacc    2880
gcccagcaga ccaccaagct cgacgccccg accaacctcc agttcgtgaa cgagaccgac    2940
agcaccgtgc tcgtgcgctg gacccgccg cgcgcccaga tcaccggcta ccgcctcacc    3000
gtgggcctca cccgccgcgg ccagccgcgc cagtacaacg tgggcccgag cgtgagcaag    3060
tacccgctcc gcaacctcca gccggccagc gagtacaccg tgagcctcgt ggccatcaag    3120
ggcaaccagg agagcccgaa ggccaccggc gtgttccacca ccctccagcc gggcagcagc    3180
atcccgccgt acaacaccga ggtgaccgag accaccatcg tgatcacctg gacccccggcc    3240 ccgcgcatcg gcttcaagct cggcgtgcgc ccagccagg gcggcgaggc cccgcgcgag    3300
gtgaccagcg acagcggcag catcgtggtg agcggcctca cccgggcgt ggagtacgtg    3360 tacaccatcc aggtgctccg cgacggccag gagcgcgacg ccccgatcgt gaacaaggtg    3420 gtgacccgc tcagcccgcc gaccaacctc cacctcgaag ccaacccgga caccggcgtg    3480
ctcaccgtga gctgggagcg cagcaccacc ccggacatca ccggctaccg catcaccacc    3540
accccgacca acggccagca gggcaacagc ctcgaagagg tggtgcacgc cgaccagagc    3600
agctgcacct tcgacaacct cagcccgggc ctcgaataca acgtgagcgt gtacaccgtg    3660
aaggacgaca aggagagcgt gccgatcagc gacaccatca tcccggccgt gccgccgccg    3720
accgacctcc gcttcaccaa catcggcccc gacaccatgc gcgtgacctg gccccgccg    3780 ccgagcatcg acctcaccaa cttcctcgtg cgctacagcc cggtgaagaa cgaggaggac    3840
gtggccgagc tcagcatcag cccgagcgac aacgccgtgg tgctcaccaa cctcctcccg    3900
ggcaccgagt acgtggtgag cgtgagcagc gtgtacgagc agcacgagag caccccgctc    3960 cgcggccgc agaagaccgg cctcgacagc ccgaccggca tcgacttcag cgacatcacc    4020
gccaacagct tcaccgtgca ctggatcgcc ccgcgcgcca ccatcaccgg ctaccgcatc    4080
cgccaccacc cggagcactt cagcggccgc ccgcgcgagg accgcgtgcc gcacagccgc    4140
aacagcatca ccctcaccaa cctcaccccg ggcaccgagt acgtggtgag catcgtggcc    4200
ctcaacggcc gcgaggagag cccgctcctc atcggccagc agagcaccgt gagcgacgtg    4260
ccgcgcgacc tcgaagtggt ggccgccacc ccgaccagcc tcctcatcag ctgggacgcc    4320
ccggccgtga ccgtgcgcta ctaccgcatc acctacggcg agaccggcgg caacagcccg    4380
```

```
gtgcaggagt tcaccgtgcc gggcagcaag agcaccgcca ccatcagcgg cctcaagccg   4440
ggcgtggact acaccatcac cgtgtacgcc gtgaccggcc gcggcgacag cccggccagc   4500
agcaagccga tcagcatcaa ctaccgcacc gagatcgaca agccgagcca gatgcaggtg   4560
accgacgtgc aggacaacag catcagcgtg aagtggctcc cgagcagcag cccggtgacc   4620
ggctaccgcg tgaccaccac cccgaagaac ggcccgggcc cgaccaagac caagaccgcc   4680
ggcccggacc agaccgagat gaccatcgag ggcctccagc cgaccgtgga gtacgtggtg   4740
agcgtgtacg cccagaaccc gagcggcgag agccagccgc tcgtgcagac cgccgtgacc   4800
aacatcgacc gcccgaaggg cctcgccttc accgacgtgg acgtggacag catcaagatc   4860
gcctgggaga gccgcagggg ccaggtgagc cgctaccgcg tgacctacag cagcccggag   4920
gacggcatcc acgagctctt cccggccccg gacggcgagg aggacaccgc cgagctccag   4980
ggcctccgcc cgggcagcga gtacaccgtg agcgtggtgg ccctccacga cgacatggag   5040
agccagccgc tcatcggcac ccagagcacc gccatcccgg cccgaccga cctcaagttc   5100 acccaggtga ccccgaccag cctcagcgcc cagtggaccc cgccgaacgt gcagctcacc   5160
ggctaccgcg tgcgcgtgac cccgaaggag aagaccggcc cgatgaagga gatcaacctc   5220
gccccggaca gcagcagcgt ggtggtgagc ggcctcatgg tggccaccaa gtacgaggtg   5280
agcgtgtacg ccctcaagga caccctcacc agccgcccgg cccagggcgt ggtgaccacc   5340
ctcgaaaacg tgagcccgcc gcgccgcgcc cgcgtgaccg acgccaccga gaccaccatc   5400
accatcagct ggcgcaccaa gaccgagacc atcaccggct tccaggtgga cgccgtgccg   5460
gccaacggcc agaccccgat ccagcgcacc atcaagccgg acgtgcgcag ctacaccatc   5520
accggcctcc agccgggcac cgactacaag atctacctct acaccctcaa cgacaacgcc   5580
cgcagcagcc cggtggtgat cgacgccagc accgccatcg acgccccgag caactga      5637
```

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
atcaactacc gcaccgagat                                                20

<210> SEQ ID NO 3
<211> LENGTH: 19
<212> TYPE: DNA
<213> ORGANISM: Artificial
<220> FEATURE:
<223> OTHER INFORMATION: Primer

<400> SEQUENCE: 3
tcttctcctt cggggtcac                                                 19

METHOD FOR SEPARATING AND PURIFYING RECOMBINANT HUMAN FIBRONECTIN FROM GENETICALLY ENGINEERED RICE SEED

RELATED APPLICATIONS

This application is a national phase application claiming benefit of priority under 35 U.S.C. § 371 to International (PCT) Patent Application serial number PCT/CN2019/123762, filed Dec. 6, 2019, which claims benefit of priority to Chinese Patent Application No. CN 201811505129.2, filed Dec. 10, 2018. The aforementioned applications are expressly incorporated herein by reference in their entirety and for all purposes.

FIELD OF THE INVENTION

The invention belongs to the field of biotechnology, and particularly relates to a method for separating and purifying recombinant human fibronectin.

BACKGROUND OF THE INVENTION

Fibronectin (Fn), also known as fibronectin, is a high molecular weight glycoprotein that is extremely widely distributed in plasma, intracellular substances and various cell surfaces, and usually exists in the form of a dimer with a molecular weight of about 450 kD with a disulfide bond located at the carboxyl end of the protein, while the molecular weight of monomer is about 220-250 kD. Fibronectin is mostly present in a soluble form in body fluids such as plasma, and in an insoluble form in the extracellular matrix. It can be combined with extracellular matrix proteins such as collagen, circulating blood proteins, fibrin, glycosaminoglycans and heparin etc. Therefore, it plays an significant role in many important physiological processes such as embryonic development, wound healing, hemostasis and coagulation.

Primarily the method of purifying Fn from tissues was mostly cryoprecipitation. Fn and some impurity proteins can be co-precipitated when left standing below 4° C., and then further purified by methods such as precipitation combined with ion exchange chromatography; while preparation of Fn from the surface of the cultured fibrin usually used a low-concentration urea; and an anti-Fn resin may be widely used in the purification of Fn in plasma and cell culture. However, these methods are gradually replaced by affinity chromatography based on the characters of specific affinity to bind to denatured collagen (usually gelatin), and then could be eluted with 1 mol L KBr and 1-8 mol L urea or amine salt.

The content of fibronectin is extremely rich in plasma, estimating about 300 mg/L. Therefore, plasma is a major source of preparation of Fn. The Fn products produced abroad are almost extracted from human plasma. It is widely used at cosmetic additives, alternatively could be used in medicines to treat wounds, burns and shocks etc., It shows Fn have significant social benefits and economic value. However, the limited source of plasma and the complicated production process is the hinders for large-scale production.

SUMMARY OF THE INVENTION

A objective of the present invention is to provide a chromatographic method for separating and purifying recombinant human fibronectin from genetically engineered rice seeds t expressing recombinant human fibronectin.

In order to achieve the above objective, the present invention provides the following technical solutions:

A method for separating and purifying recombinant human fibronectin from genetically engineered rice seeds, comprising the following steps:
1) extracting the recombinant human fibronectin from genetically engineered rice seeds to obtain crude extract containing recombinant human fibronectin;
2) subjecting the crude extract containing recombinant human fibronectin to cation exchange chromatography, to obtain a primary product;
3) subjecting the primary product to anion exchange chromatography, to obtain purified recombinant human fibronectin.

In the step 1), the genetically engineered rice seeds containing recombinant human fibronectin are used as raw material, the rice grains (rice seeds) are dehulled and polished into semi-polished rice and ground into rice powder with a fineness of 80-100 mesh; the rice powder is mixed with an extraction buffer at a weight/volume ratio of 1:5-1:10, extracted for 0.5-2 hours at room temperature to obtain a crude protein extract;

the extraction buffer comprises: 0-50 mM Tris-HCl, 0-50 mM PB, 0-110 mM NaCl, pH 5.9-8.0; preferably the extraction buffer comprises one or more components of 0.8-1 mM PMSF, or 5-10 mM GSH, or 0.05-0.1% Tween 80.

In the step 2), a resin for cation exchange chromatography is selected from the group consisting of NanoGel 30/50 SP, UniGel 30/80 SP, SP Bestarose FF, SP Bestarose HP, Bestarose Diamond MMC, Uniphere S, MacroPrep S, POROS XS, SP-6FF, SP-6HP, SP Sepharose™ Fast Flow. NanoGel 50 SP or SP Bestarose HP is preferred. In the cation exchange chromatography, pH gradient elution or sodium chloride concentration gradient elution may be selected, and sodium chloride gradient elution is preferred.

In one embodiment, the elution is performed by the way of combination of pH and sodium chloride gradient. Impurity-washing buffer comprises phosphate buffer, 0.13M sodium chloride, 0.3M sodium chloride, pH 5.9, and elution buffer comprises phosphate buffer, 0.1M sodium chloride, 0.3M sodium chloride, pH 7.0.

In another embodiment, sodium chloride gradient elution is selected, and the impurity-washing and elution buffer in the chromatographic process comprises phosphate buffer, 0.15M sodium chloride, 0.3M sodium chloride, pH 7.0.

In the step 3), a resin for anion exchange chromatography is selected from the group consisting of Q Bestarose Fast Flow, Q Bestarose HP, Bestarose DEAE, Q Sepharose™ HP, Q Sepharose™ Fast Flow, DEAE Sepharose™ Fast Flow, UniGel 30/80Q, NanoGel 30/50Q, UNO Sphere Q. BLG Q FF (Bestchrom) or HY Q HP (Huiyan) is preferred.

Sodium chloride concentration gradient elution may be selected in the anion exchange chromatography. In one embodiment, the impurity-washing and elution buffer in the chromatographic process comprises a phosphate buffer, 0.2M sodium chloride, 0.3M sodium chloride, both pH 7.0.

The target protein elution fractions obtained by anion exchange chromatography may be concentrated, freeze-dried etc., by known methods to make into finished products.

In cation exchange chromatography, the loading buffer comprises a phosphate buffer, having a pH of less than 7.5, a salt concentration of less than 0.12M.

The elution buffer for the target protein (recombinant human fibronectin) in cation exchange chromatography comprises a phosphate buffer and sodium chloride; pH 6.8-7.1. Preferably, the sodium chloride concentration is 0.3M, and the pH of the buffer is 7.0.

In one embodiment, when the cation exchange chromatography is SP Bestarose HP, the buffer used comprises phosphate buffer, 0.09-0.13M sodium chloride, pH 5.8-7.1.

In another embodiment, when the cation exchange chromatography is Nano Gel 50 SP, the buffer used comprises phosphate buffer, 0.12-0.3M sodium chloride, pH 6.8-7.1.

In another embodiment, when the anion exchange chromatography is HY Q HP (Huiyan), the buffer used comprises phosphate, 0.1-0.3M sodium chloride, pH 6.8-7.1.

In another embodiment, when the anion exchange chromatography is BLG Q FF (Bestchrom), the buffer used comprises phosphate, 0.1-0.3M sodium chloride, pH 6.8-7.1.

The present invention also provides a plant expression vector for preparing the genetically engineered rice seeds. The expression vector is constructed by introducing the gene expressing human fibronectin, a rice endosperm-specific promoter Gt13a and its signal peptide. Preferably, the gene encoding the human fibronectin has the nucleotide sequence as shown in SEQ ID NO. 1, and the plasmid vector is pOsPMP626.

The raw materials used in the present invention are derived from genetically engineered rice grains that express recombinant fibronectin. Fn is synthesized and entered the inner membrane system of rice endosperm cells driven by the endosperm-specific promoter and signal peptides, finally OsrFn is stored in the protein body of rice endosperm to largely accumulate in rice grains. Due to no plasma-specific impurities such as Fg and vWF in the rice grain, the purification method is different compared to other sources. It exhibits great advantages at the separation and purification of Fn from the rice seeds.

The invention uses a two-step chromatography of cation and anion exchange to separate and purify Fn from genetically engineered rice seeds that express recombinant fibronectin, explores and optimizes the process parameters that the purification processing could scaled up.

DETAILED DESCRIPTION OF THE INVENTION

Hereinafter, the technical solutions of the present invention will be described through examples and figures to illustrate the characteristics and the advantages of the present invention in detail. The examples provided here should be construed as exemplary of the method of the present invention, and do not limit the technical solutions disclosed by the present invention in any way.

The reagents and instruments used in the following examples are all commercially available unless otherwise specified.

Figure 1:
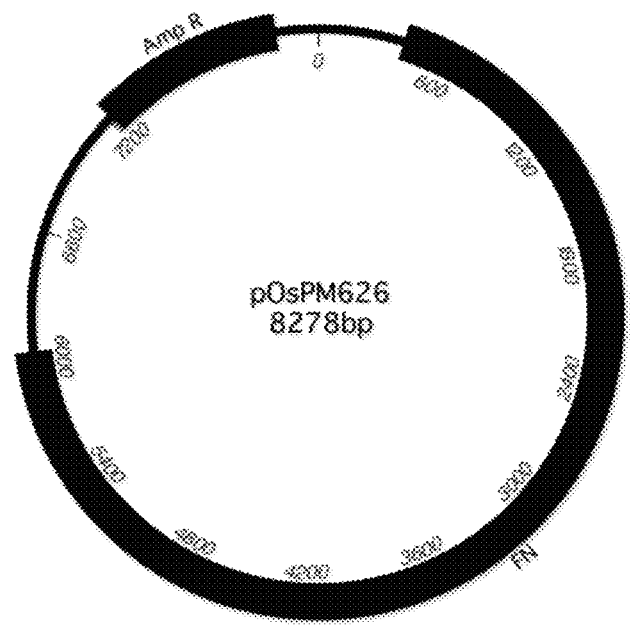
FIG. 1 is a schematic diagram of the structure of plasmid pOsPMP626.
Figure 2:
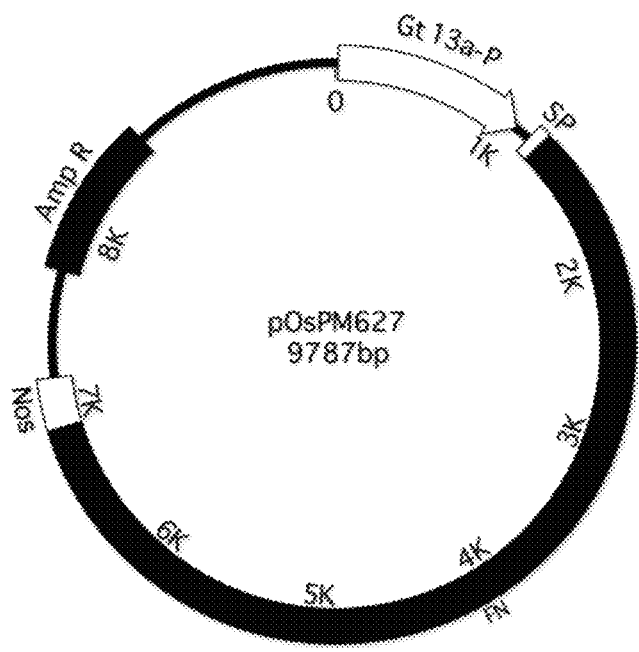
FIG. 2 is a schematic diagram of the structure of plasmid pOsPMP627.
Figure 3:
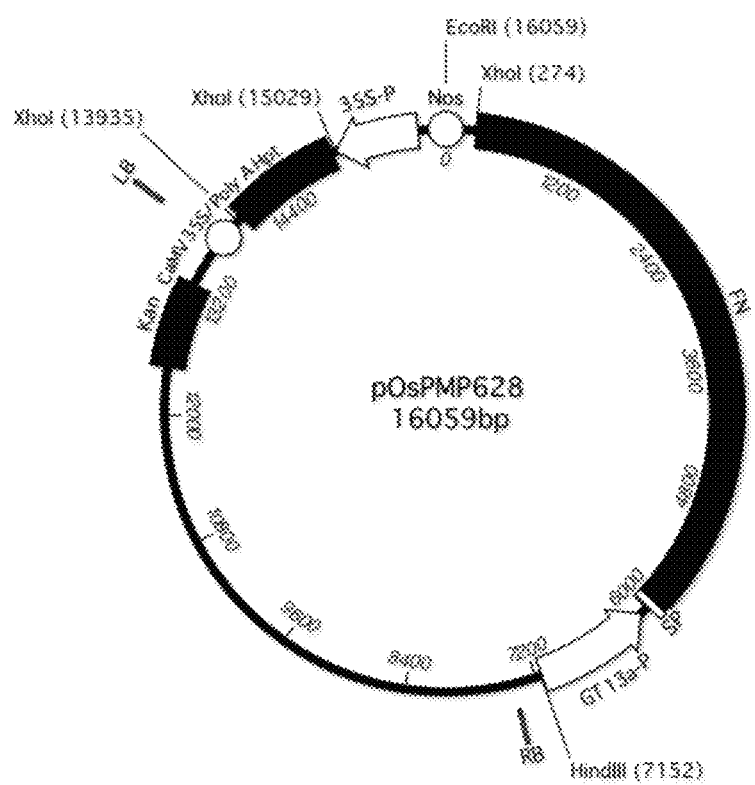
FIG. 3 is a schematic diagram of the structure of plasmid pOsPMP628.
Figure 4:
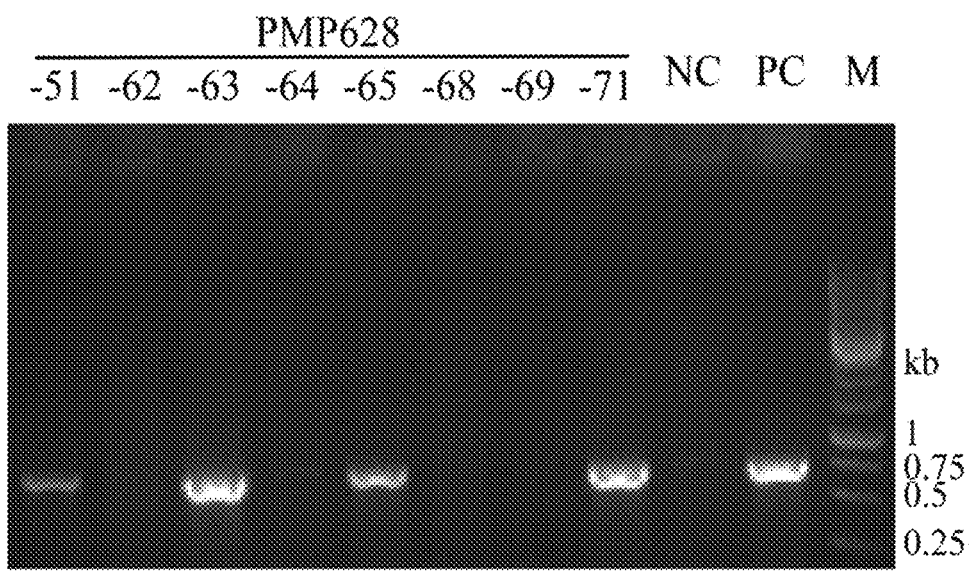
FIG. 4 shows the PCR results for target genes in the T1 generation of genetically engineered materials, where: M, DNA standard molecular weight Marker; PMP628-51, 628-62, 628-63, 628-64, 628-65, 628-68, 628-69 and 628-71 are the T1 generation transgenic materials; NC, negative control recipient species; P, positive control plasmid.
Figure 5:
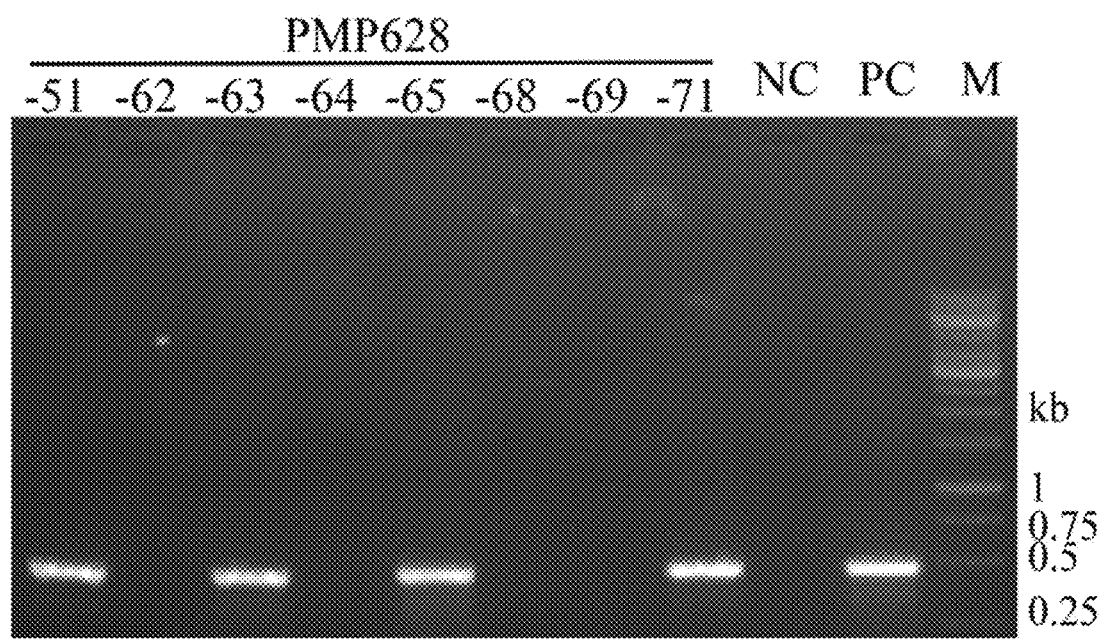
FIG. 5 shows the PCR results for detection of marker genes in the T1 generation of genetically engineered rice leaves, where: M, DNA standard molecular weight Marker; PMP628-51, 628-62, 628-63, 628-64, 628-65, 628-68, 628-69 and 628-71 are the T1 generation genetically engineered materials; NC, negative control recipient species; P, positive control plasmid.

Example 1: Preparation of Genetically Engineered Rice Containing Recombinant Human Fibronectin Expression Cassette In this example, a rice-specific promoter Gt13a and its signal peptide were used to drive the expression of recombinant human fibronectin genes in rice endosperm cells. For details, refer to the method in the publication number CN100540667 to construct the vector of recombinant human fibronectin specifically expressed in rice of the present invention and select genetically engineered rice plants, where the recombinant human serum albumin gene was replaced with the recombinant human fibronectin gene of the invention. As shown in FIG. 1, a plasmid designated pOsPMP626 was used to construct a rice endosperm-specific expression cassette. The synthetic codon-optimized human FN genes (SEQ ID NO. 1) were digested with MyII and XhoI and cloned into pOsPMP02 to construct a plasmid pOsPMP627 (FIG. 2); then pOsPMP627 was digested with HindIII and EcoRI, the entire expression cassette with a length of 7152 bp containing the Gt13a promoter, signal peptide sequence, codon-optimized FN gene and Nos terminator was inserted into the binary expression vector p1300 to produce an agrobacterium-mediated plasmid, designated as pOsPMP628 (FIG. 3). The pOsPMP628 plasmid was transformed into *Agrobacterium tumefaciens* EHA105 (Invitrogen, the USA) through co-transformation via the *Agrobacterium tumefaciens*-mediated into the callus regeneration tissue of rice variety TP309. After cultivated, screened and induced to form a complete plantlets; The Hpt resistant plantlet identified by PCR using target gene-specific primer pair the forward primer FN-F1 (SEQ ID NO. 2: 5'-ATCAACTACCGCACCGAGAT-3') and the reverse primer FN-R1 (SEQ ID NO.3: 5'-TCTTCTCCTTCGGGGT-CAC-3'). The PCR product size was 679 bp. There were four independent transformants were identified to highly express recombinant human fibronectin from 72 independent transformants. The identification results are shown in FIG. 4 and FIG. 5.

Figure 6:
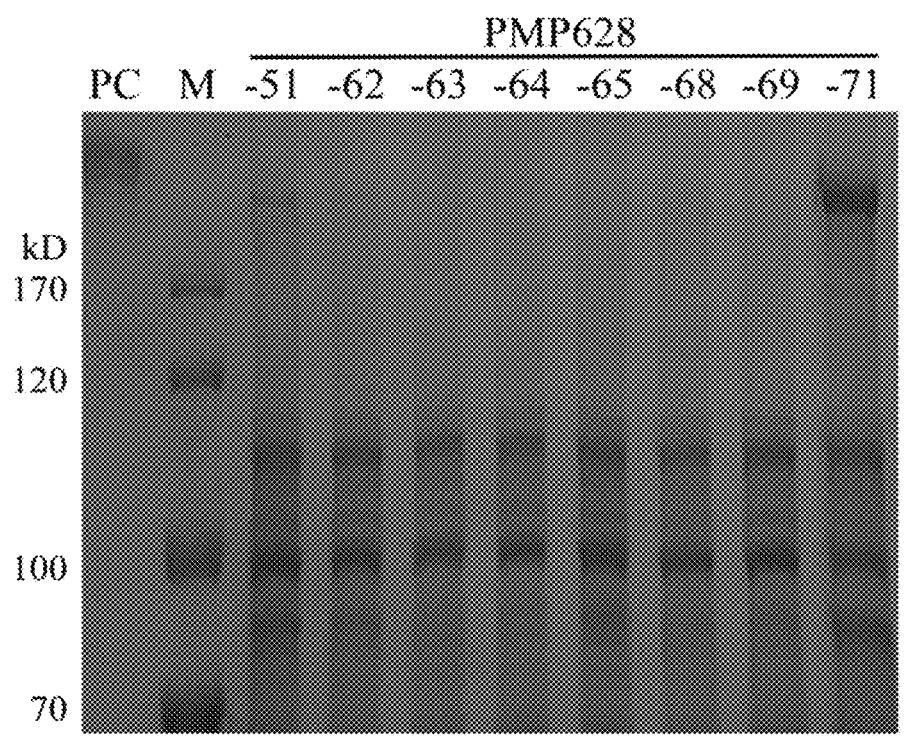
FIG. 6 shows the SDS-PAGE image for detection of FN expressed in T1 genetically engineered seeds, where: M, standard molecular weight Marker; PC, 220 kD Human Plasma Fibronectin (FN) pure protein (Merck); PMP628-51, 628-62, 628-63, 628-64, 628-65, 628-68, 628-69 and 628-71 are transgenic lines.

In this example, the expression level of OsrhFn in the above four genetically engineered rice plants was determined by SDS-PAGE. The results showed that the highest line of expressing FN was PMP628-71 as shown in FIG. 6. Through the above multiple detection methods, a genetically stable engineered rice plants were selected.

SEQ ID NO. 1

```
ATGCAGGCCC AGCAGATGGT GCAGCCGCAG AGCCCGGTGG CCGTGAGCCA GAGCAAGCCG   60

GGCTGCTACG ACAACGGCAA GCACTACCAG ATCAACCAGC AGTGGGAGCG CACCTACCTC  120

GGCAACGCCC TCGTGTGCAC CTGCTACGGC GGCAGCCGCG GCTTCAACTG CGAGAGCAAG  180

CCGGAGGCCG AGGAGACCTG CTTCGACAAG TACACCGGCA ACACCTACCG CGTGGGCGAC  240

ACCTACGAGC GCCCGAAGGA CAGCATGATC TGGGACTGCA CCTGCATCGG CGCCGGCCGC  300

GGCCGCATCA GCTGCACCAT CGCCAACCGC TGCCACGAGG CGGCCAGAG CTACAAGATC  360

GGCGACACCT GGCGCCGCCC GCACGAGACC GGCGGCTACA TGCTCGAATG CGTGTGCCTC  420

GGCAACGGCA AGGGCGAGTG GACCTGCAAG CCGATCGCCG AGAAGTGCTT CGACCACGCC  480

GCCGGCACCA GCTACGTGGT GGGCGAGACC TGGGAGAAGC CGTACCAGGG CTGGATGATG  540

GTGGACTGCA CCTGCCTCGG CGAGGGCAGC GGCCGCATCA CCTGCACCAG CCGCAACCGC  600

TGCAACGACC AGGACACCCG CACCAGCTAC CGCATCGGCG ACACCTGGAG CAAGAAGGAC  660

AACCGCGGCA ACCTCCTCCA GTGCATCTGC ACCGGCAACG GCCGCGGCGA GTGGAAGTGC  720

GAGCGCCACA CCAGCGTGCA GACCACCAGC AGCGGCAGCG GCCCGTTCAC CGACGTGCGC  780

GCCGCCGTGT ACCAGCCGCA GCCGCACCCG CAGCCGCCGC CGTACGGCCA CTGCGTGACC  840
```

```
GACAGCGGCG TGGTGTACAG CGTGGGCATG CAGTGGCTCA AGACCCAGGG CAACAAGCAG   900
ATGCTCTGCA CCTGCCTCGG CAACGGCGTG AGCTGCCAGG AGACCGCCGT GACCCAGACC   960
TACGGCGGCA ACAGCAACGG CGAGCCGTGC GTGCTCCCGT TCACCTACAA CGGCCGCACC  1020
TTCTACAGCT GCACCACCGA GGGCCGCCAG GACGGCCACC TCTGGTGCAG CACCACCAGC  1080
AACTACGAGC AGGACCAGAA GTACAGCTTC TGCACCGACC ACACCGTGCT CGTGCAGACC  1140
CGCGGCGGCA ACAGCAACGG CGCCCTCTGC CACTTCCCGT TCCTCTACAA CAACCACAAC  1200
TACACCGACT GCACCAGCGA GGGCCGCCGC GACAACATGA AGTGGTGCGG CACCACCCAG  1260
AACTACGACG CCGACCAGAA GTTCGGCTTC TGCCCGATGG CCGCCCACGA GGAGATCTGC  1320
ACCACCAACG AGGGCGTGAT GTACCGCATC GGCGACCAGT GGGACAAGCA GCACGACATG  1380
GGCCACATGA TGCGCTGCAC CTGCGTGGGC AACGGCCGCG GCGAGTGGAC CTGCATCGCC  1440
TACAGCCAGC TCCGCGACCA GTGCATCGTG GACGACATCA CCTACAACGT GAACGACACC  1500
TTCCACAAGC GCCACGAGGA GGGCCACATG CTCAACTGCA CCTGCTTCGG CCAGGGCCGC  1560
GGCCGCTGGA AGTGCGACCC GGTGGACCAG TGCCAGGACA GCGAGACCGG CACCTTCTAC  1620
CAGATCGGCG ACAGCTGGGA GAAGTACGTG CACGGCGTGC GCTACCAGTG CTACTGCTAC  1680
GGCCGCGGCA TCGGCGAGTG GCACTGCCAG CCGCTCCAGA CCTACCCGAG CAGCAGCGGC  1740
CCGGTGGAGG TGTTCATCAC CGAGACCCCG AGCCAGCCGA ACAGCCACCC GATCCAGTGG  1800
AACGCCCCGC AGCCGAGCCA CATCAGCAAG TACATCCTCC GCTGGCGCCC GAAGAACAGC  1860
GTGGGCCGCT GGAAGGAGGC CACCATCCCG GGCCACCTCA ACAGCTACAC CATCAAGGGC  1920
CTCAAGCCGG GCGTGGTGTA CGAGGGCCAG CTCATCAGCA TCCAGCAGTA CGGCCACCAG  1980
GAGGTGACCC GCTTCGACTT CACCACCACC AGCACCAGCA CCCCGGTGAC CAGCAACACC  2040
GTGACCGGCG AGACCACCCC GTTCAGCCCG CTCGTGGCCA CCAGCGAGAG CGTGACCGAG  2100
ATCACCGCCA GCAGCTTCGT GGTGAGCTGG GTGAGCGCCA GCGACACCGT GAGCGGCTTC  2160
CGCGTGGAGT ACGAGCTCAG CGAGGAGGGC GACGAGCCGC AGTACCTCGA CCTCCCGAGC  2220
ACCGCCACCA GCGTGAACAT CCCGGACCTC CTCCCGGGCC GCAAGTACAT CGTGAACGTG  2280
TACCAGATCA GCGAGGACGG CGAGCAGAGC CTCATCCTCA GCACCAGCCA GACCACCGCC  2340
CCGGACGCCC CGCCGGACAC CACCGTGGAC CAGGTGGACG ACACCAGCAT CGTGGTGCGC  2400
TGGAGCCGCC CGCAGGCCCC GATCACCGGC TACCGCATCG TGTACAGCCC GAGCGTGGAG  2460
GGCAGCAGCA CCGAGCTCAA CCTCCCGGAG ACCGCCAACA GCGTGACCCT CAGCGACCTC  2520
CAGCCGGGCG TGCAGTACAA CATCACCATC TACGCCGTGG AGGAGAACCA GGAGAGCACC  2580
CCGGTGGTGA TCCAGCAGGA GACCACCGGC ACCCCGCGCA GCGACACCGT GCCGAGCCCG  2640
CGCGACCTCC AGTTCGTGGA GGTGACCGAC GTGAAGGTGA CCATCATGTG GACCCCGCCG  2700
GAGAGCGCCG TGACCGGCTA CCGCGTGGAC GTGATCCCGG TGAACCTCCC GGGCGAGCAC  2760
GGCCAGCGCC TCCCGATCAG CCGCAACACC TTCGCCGAGG TGACCGGCCT CAGCCCGGGC  2820
GTGACCTACT ACTTCAAGGT GTTCGCCGTG AGCCACGGCC GCGAGAGCAA GCCGCTCACC  2880
GCCCAGCAGA CCACCAAGCT CGACGCCCCG ACCAACCTCC AGTTCGTGAA CGAGACCGAC  2940
AGCACCGTGC TCGTGCGCTG GACCCCGCCG CGCGCCCAGA TCACCGGCTA CCGCCTCACC  3000
GTGGGCCTCA CCCGCCGCGG CCAGCCGCGC CAGTACAACG TGGGCCCGAG CGTGAGCAAG  3060
TACCCGCTCC GCAACCTCCA GCCGGCCAGC GAGTACACCG TGAGCCTCGT GGCCATCAAG  3120
GGCAACCAGG AGAGCCCGAA GGCCACCGGC GTGTTCACCA CCCTCCAGCC GGGCAGCAGC  3180
ATCCCGCCGT ACAACACCGA GGTGACCGAG ACCACCATCG TGATCACCTG GACCCCGGCC  3240
```

```
CCGCGCATCG GCTTCAAGCT CGGCGTGCGC CCGAGCCAGG GCGGCGAGGC CCCGCGCGAG    3300

GTGACCAGCG ACAGCGGCAG CATCGTGGTG AGCGGCCTCA CCCCGGGCGT GGAGTACGTG    3360

TACACCATCC AGGTGCTCCG CGACGGCCAG GAGCGCGACG CCCCGATCGT GAACAAGGTG    3420

GTGACCCCGC TCAGCCCGCC GACCAACCTC CACCTCGAAG CCAACCCGGA CACCGGCGTG    3480

CTCACCGTGA GCTGGGAGCG CAGCACCACC CCGGACATCA CCGGCTACCG CATCACCACC    3540

ACCCCGACCA ACGGCCAGCA GGGCAACAGC CTCGAAGAGG TGGTGCACGC CGACCAGAGC    3600

AGCTGCACCT TCGACAACCT CAGCCCGGGC CTCGAATACA ACGTGAGCGT GTACACCGTG    3660

AAGGACGACA AGGAGAGCGT GCCGATCAGC GACACCATCA TCCCGGCCGT GCCGCCGCCG    3720

ACCGACCTCC GCTTCACCAA CATCGGCCCG GACACCATGC GCGTGACCTG GCCCCGCCG    3780

CCGAGCATCG ACCTCACCAA CTTCCTCGTG CGCTACAGCC CGGTGAAGAA CGAGGAGGAC    3840

GTGGCCGAGC TCAGCATCAG CCCGAGCGAC AACGCCGTGG TGCTCACCAA CCTCCTCCCG    3900

GGCACCGAGT ACGTGGTGAG CGTGAGCAGC GTGTACGAGC AGCACGAGAG CACCCCGCTC    3960

CGCGGCCGCC AGAAGACCGG CCTCGACAGC CCGACCGGCA TCGACTTCAG CGACATCACC    4020

GCCAACAGCT TCACCGTGCA CTGGATCGCC CCGCGCGCCA CCATCACCGG CTACCGCATC    4080

CGCCACCACC CGGAGCACTT CAGCGGCCGC CCGCGCGAGG ACCGCGTGCC GCACAGCCGC    4140

AACAGCATCA CCCTCACCAA CCTCACCCCG GGCACCGAGT ACGTGGTGAG CATCGTGGCC    4200

CTCAACGGCC GCGAGGAGAG CCCGCTCCTC ATCGGCCAGC AGAGCACCGT GAGCGACGTG    4260

CCGCGCGACC TCGAAGTGGT GGCCGCCACC CCGACCAGCC TCCTCATCAG CTGGGACGCC    4320

CCGGCCGTGA CCGTGCGCTA CTACCGCATC ACCTACGGCG AGACCGGCGG CAACAGCCCG    4380

GTGCAGGAGT TCACCGTGCC GGGCAGCAAG AGCACCGCCA CCATCAGCGG CCTCAAGCCG    4440

GGCGTGGACT ACACCATCAC CGTGTACGCC GTGACCGGCC GCGGCGACAG CCCGGCCAGC    4500

AGCAAGCCGA TCAGCATCAA CTACCGCACC GAGATCGACA AGCCGAGCCA GATGCAGGTG    4560

ACCGACGTGC AGGACAACAG CATCAGCGTG AAGTGGCTCC CGAGCAGCAG CCCGGTGACC    4620

GGCTACCGCG TGACCACCAC CCCGAAGAAC GGCCCGGGCC CGACCAAGAC CAAGACCGCC    4680

GGCCCGGACC AGACCGAGAT GACCATCGAG GGCCTCCAGC CGACCGTGGA GTACGTGGTG    4740

AGCGTGTACG CCCAGAACCC GAGCGGCGAG AGCCAGCCGC TCGTGCAGAC CGCCGTGACC    4800

AACATCGACC GCCCGAAGGG CCTCGCCTTC ACCGACGTGG ACGTGGACAG CATCAAGATC    4860

GCCTGGGAGA GCCCGCAGGG CCAGGTGAGC CGCTACCGCG TGACCTACAG CAGCCCGGAG    4920

GACGGCATCC ACGAGCTCTT CCCGGCCCCG GACGGCGAGG AGGACACCGC CGAGCTCCAG    4980

GGCCTCCGCC CGGGCAGCGA GTACACCGTG AGCGTGGTGG CCCTCCACGA CGACATGGAG    5040

AGCCAGCCGC TCATCGGCAC CCAGAGCACC GCCATCCCGG CCCCGACCGA CCTCAAGTTC    5100

ACCCAGGTGA CCCCGACCAG CCTCAGCGCC CAGTGGACCC CGCCGAACGT GCAGCTCACC    5160

GGCTACCGCG TGCGCGTGAC CCCGAAGGAG AAGACCGGCC CGATGAAGGA GATCAACCTC    5220

GCCCCGGACA GCAGCAGCGT GGTGGTGAGC GGCCTCATGG TGGCCACCAA GTACGAGGTG    5280

AGCGTGTACG CCCTCAAGGA CACCCTCACC AGCCGCCCGG CCCAGGGCGT GGTGACCACC    5340

CTCGAAAACG TGAGCCCGCC GCGCCGCGCC CGCGTGACCG ACGCCACCGA GACCACCATC    5400

ACCATCAGCT GGCGCACCAA GACCGAGACC ATCACCGGCT TCCAGGTGGA CGCCGTGCCG    5460

GCCAACGGCC AGACCCCGAT CCAGCGCACC ATCAAGCCGG ACGTGCGCAG CTACACCATC    5520

ACCGGCCTCC AGCCGGGCAC CGACTACAAG ATCTACCTCT ACACCCTCAA CGACAACGCC    5580

CGCAGCAGCC CGGTGGTGAT CGACGCCAGC ACCGCCATCG ACGCCCCGAG CAACTGA      5637
```

Example 2: Extraction of Crude Extract of Recombinant Human Fibronectin(hFn) from Gene Engineered Rice Grain The genetically engineered rice grain containing recombinant human fibronectin was hulled and polished into semi-polished rice, and ground to powder with a fineness of 80-100 mesh. The rice powder was mixed with an extraction buffer at a ratio of 1:5 (w/v, kg/L), and extracted at room temperature for 1 hour. The extraction buffer comprises: 20 mM sodium phosphate (PB), pH 8.0, 5 mM glutathione, 1 mM PMSF, and 0.1% Tween 80. The mixture was clarified through a cloth filter press. The glutathione, PMSF and Tween 80 in extraction buffer could improve the extraction efficiency, prevent from degradation and reduce dimers and multimers during extraction procedure.

Example 3: Development of Small-Scale Purification Processing of OsrhFn

Figure 7:
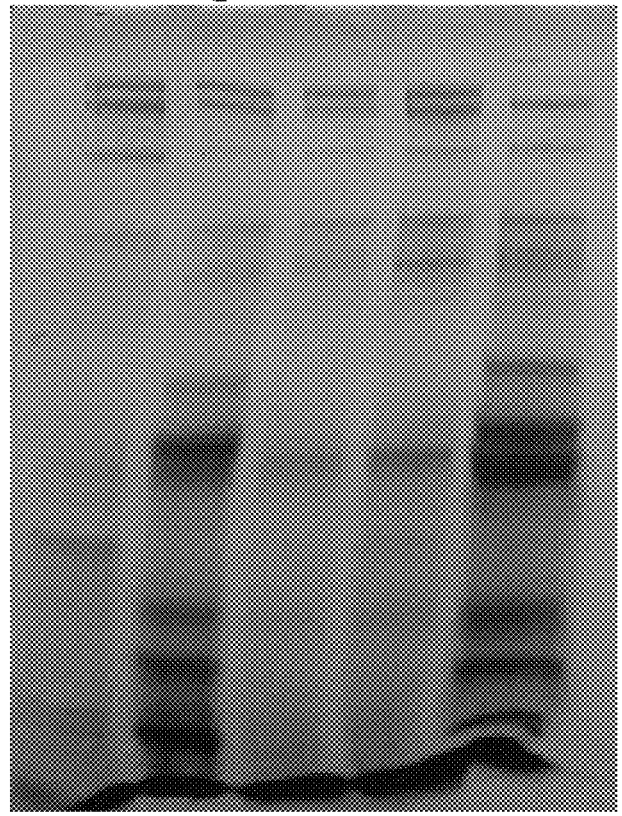
FIG. 7 shows the SDS-PAGE image for detection of the OsrFn eluted by different processing parameters of Heparin affinity chromatography, where: Nanomicro, Qianchun, Bestchrom, GE, and Huiyan company correspond to NW, QC, BGL, GE, and HY, respectively.

1. Development of Primary Purification Parameters of OsrhFn 1.1 Selection of Affinity Chromatographic Media and Development of Chromatographic Parameters In the present invention, different types of Heparin affinity resins from five vendors, including Nanomicro, Qianchun, Bestchrom, G E, and Huiyan, were compared and developing primary purification processes. The eluents of different Heparin affinity resins were obtained. The final eluents were detected by SDS-PAGE. The results are shown in FIG. 7.

Figure 8:
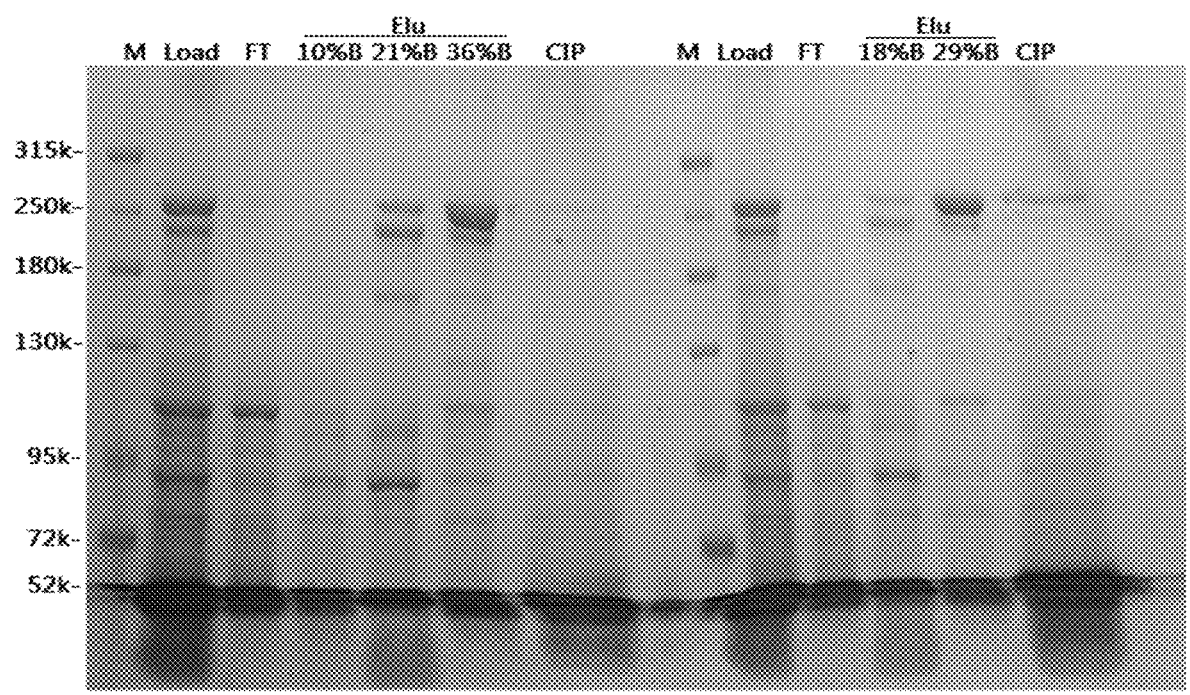
FIG. 8 shows the SDS-PAGE image for detection of the OsrFN by optimized washing step of Heparin chromatography, where: M, standard molecular weight Maker; Load, protein extract; FT, flow-through solution; 10% B, 100 mM NaCl; 18% B, 21% B, 29% B, 36% B correspond to 180 mM, 210 mM, 290 mM, 360 mM NaCl, respectively.
Figure 9:
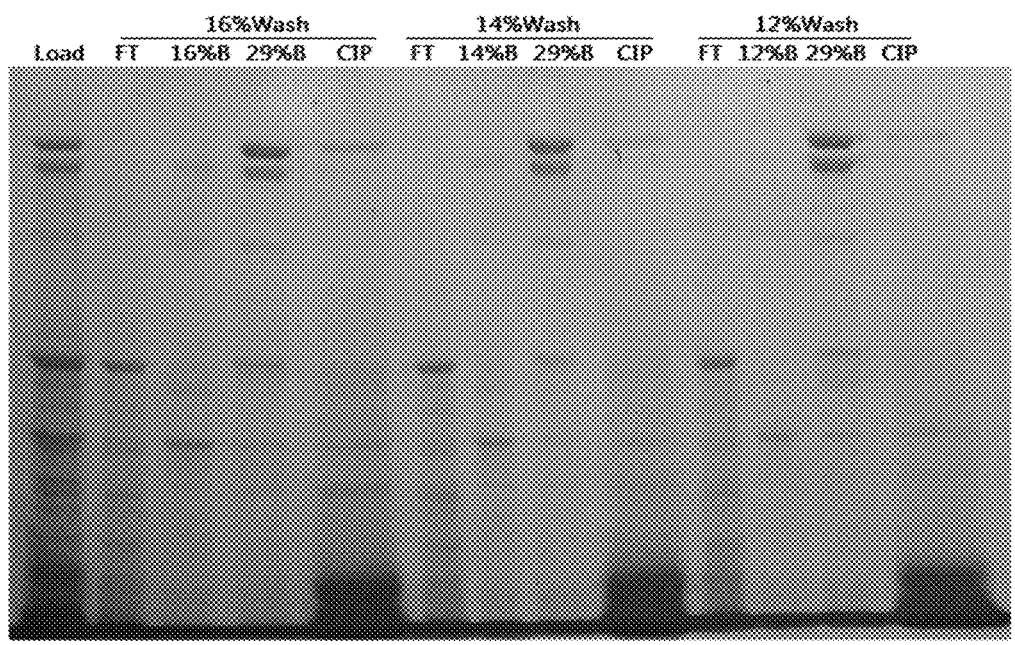
FIG. 9 shows the SDS-PAGE image for detection of the OsrFN by optimized washing step of Heparin chromatography, where: Load, protein extract, FT, flow-through solution; 12% B, 14% B, 16% B, 29% B correspond to 120 mM, 140 mM, 160 mM, 290 mM NaCl; CIP (clean-in-place): regenerated solution.

By comparison, it was found that the Heparin resins from the three vendors, Nanomicro, Bestchrom, and GE had better purification performance. The resin from Nanomicro was more suitable as the chromatographic resin to the capture step based on its basic frame of polystyrene, and stability and repeatability. According to the analysis on the purification parameters, Heparin do not reduce non-specific adsorption, furthermore there is large amount of target protein was lost under high-salt conditions. Therefore, loading buffer with low-salt were selected for loading. And then a impurity-washing step were developed. The different salt concentrations in washing buffer were optimized from 100-180 mM NaCl with pH 8.0. Finally, optimal salt concentration for elution was 290 mM NaCl with pH 8.0. Finally, the optimal conditions for Heparin chromatography was 120 mM NaCl, and the elution condition was 290 mM NaCl. The results from optimized purification parameters are shown in FIG. 8 and FIG. 9.

1.2 Selection of Anion Chromatographic Resin and Optimization of Chromatographic Conditions as Primary Purification Although Heparin is affinity chromatography, it is mainly characterized as ion exchange behave. it could be replaced of anion exchange chromatography according to previous studies of Heparin affinity chromatography and anion exchange chromatography. We studied 37 kinds of anionic resins, Q Bestarose Fast Flow, Q Bestarose HP, Bestarose DEAE, Q Sepharose™ HP, Q Sepharose™ Fast Flow, DEAE Sepharose™ Fast Flow, UniGel 30/80Q, NanoGel 30/50Q, UNO Sphere Q, we found that all resins can effectively enrich the target protein and simultaneously can remove certain parts of the host cell proteins.

Figure 10:
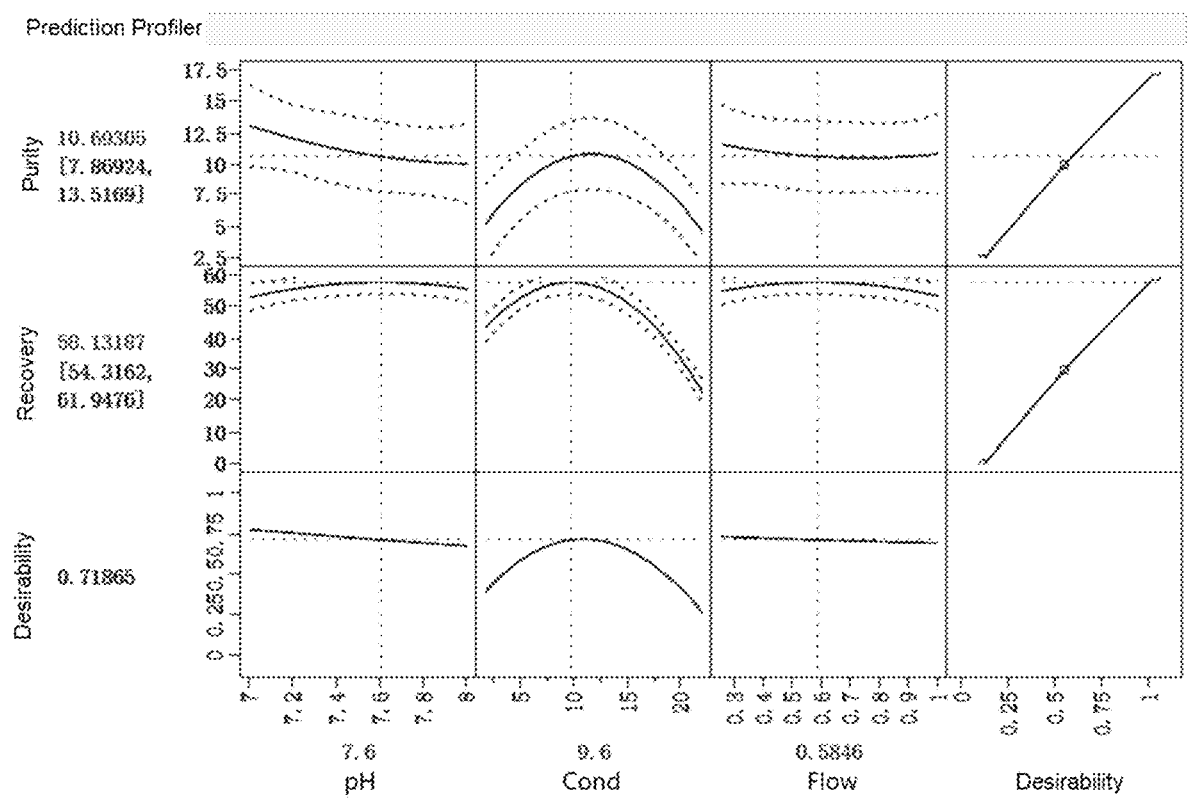
FIG. 10 shows the prediction profile for DoE experiment with different pHs, conductivity and flow rates combinations at Q FF chromatography.
Figure 11:
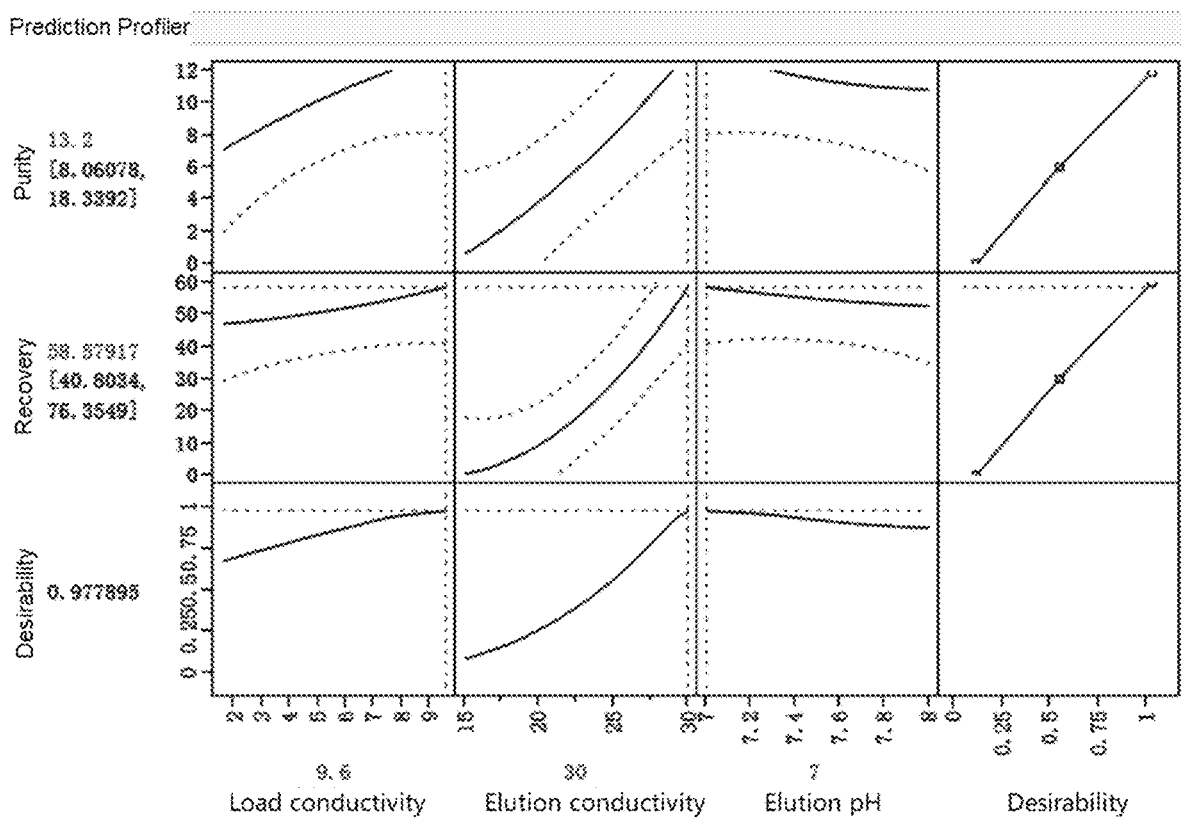
FIG. 11 shows the prediction profile for DoE experiment with different load conductivities, elution pHs, elution conductivities at HY Q FF chromatography.

The chromatographic parameters were explored when the Huiyan Q FF resin was used. The DoE was performed by combining three factors of pH value, conductivity, and flow rate, under three levels for each factor. Finally, The results showed that the optimal sample-loading parameters is: conductivity 9.6 mS/cm, pH 7.6, and flow rate 0.58 mL/min, Under these conditions, the recovery rate of OsrFn reached of 58.13%. The prediction results of the DoE are shown in FIG. 10. In order to further improve the recovery rate of Q FF, the DoE was performed by fixing the loading pH and optimizing three factors of loading conductivity, elution conductivity, and elution pH under three levels for each factor. The results showed that the loading conductivity, elution conductivity and the pH was optimized as 9.6 mS/cm, 30 mS/cm, and 7.0, respectively. The purity and maximum recovery rate of OsrFn reached 58.5% and 13.2%, respectively. The prediction results of chromatography parameters by the DoE analysis are shown in FIG. 11.

Figure 12:
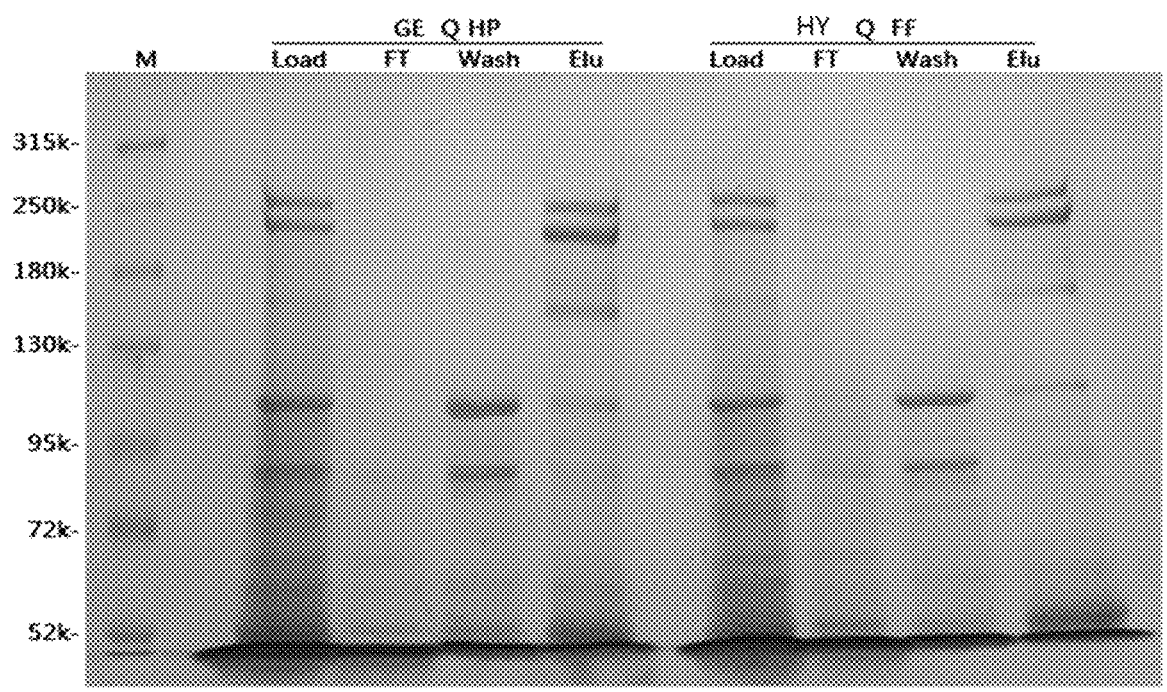
FIG. 12 shows the SDS-PAGE image for detection results of the OsrFN between GE Q HP and HY Q FF chromatography resins, where: M, standard molecular weight Marker; Load, protein extract; FT, flow-through fraction; Wash, impurity-washing fraction, and Elu, elution fraction.
Figure 13:
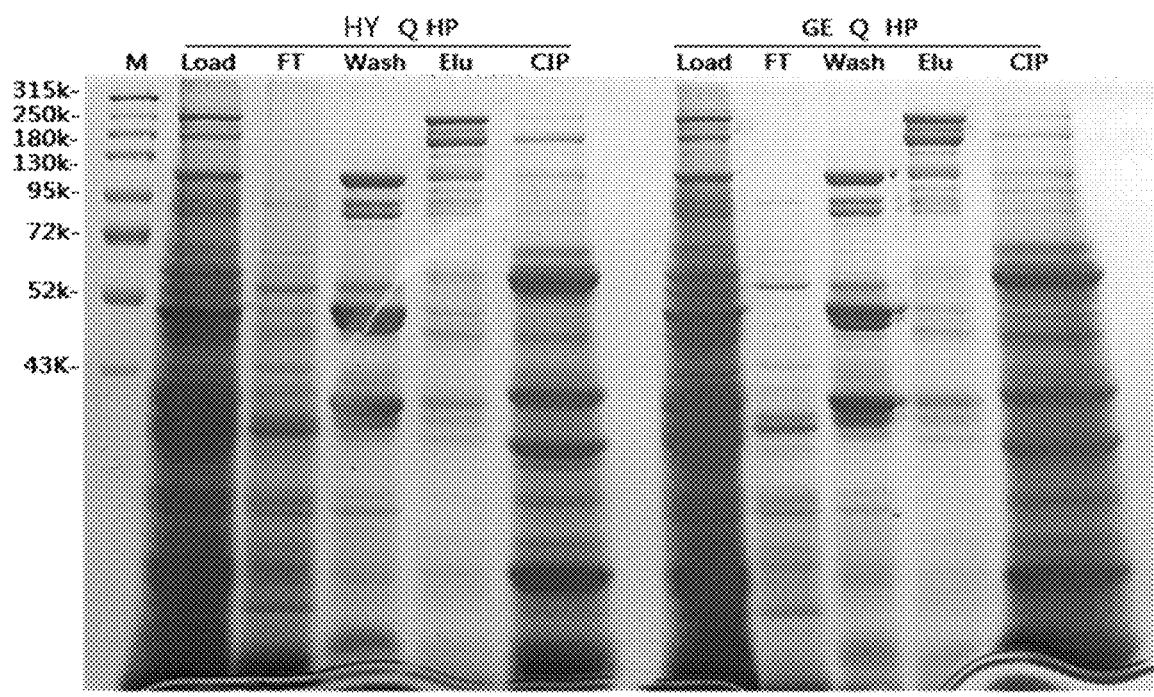
FIG. 13 shows the SDS-PAGE image for comparative results of the OsrFN between GE Q HP and HY Q HP chromatography resins, where: M, standard molecular weight Marker; Load, protein extract; FT, flow-through fraction; Wash, impurity-washing fraction, Elu, elution fraction; CIP, regenerated solution.

No matter low conductivity or high conductivity condition, certain flow through target protein was obtained using HY Q FF resin, resulting in a low recovery rate. According to the results of screening of anionic resins, HY Q HP or GE Q HP resins are suggested for further testing. As shown in FIG. 12 and FIG. 13, the optimized washing buffer comprises 50 mM Tris-HCl, 194 mM NaCl, pH 7.6, and the elution buffer comprises 50 mM Tris-HCl, 268 mM NaCl, pH 7.6.

Figure 14:
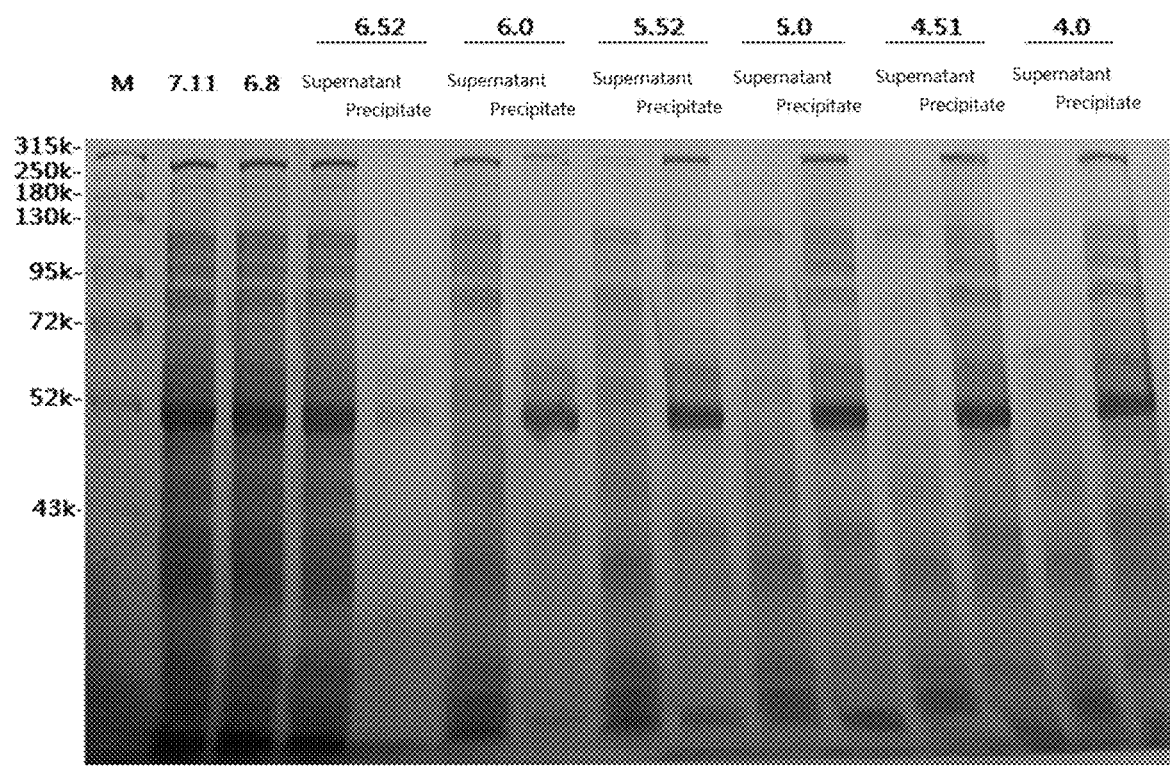
FIG. 14 shows the SDS-PAGE the results of the stability of the extract stability at different pH values, where: M, standard molecular weight Marker; Supernatant, supernatant after pH adjustment and sample centrifugation; Precipitate, redissolved solution of precipitate after pH adjustment and sample centrifugation.
Figure 15:
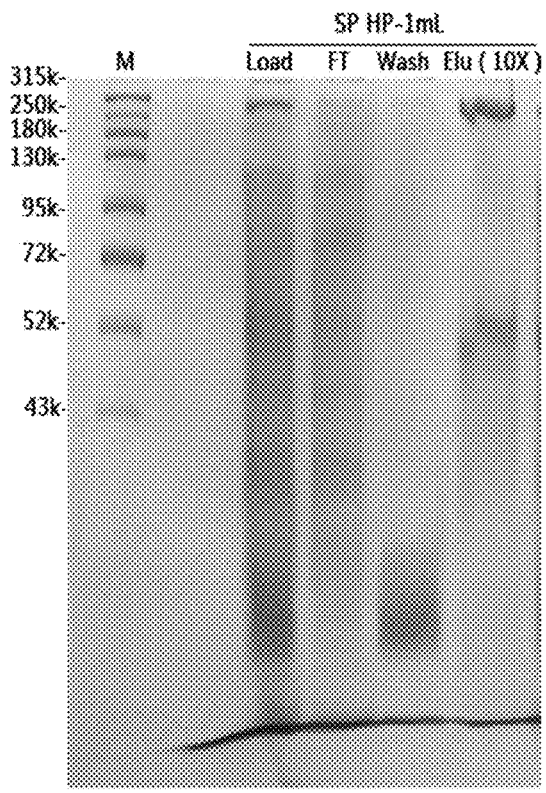
FIG. 15 shows the SDS-PAGE image of elution results of OsrFN of BGL SP HP chromatography resins, where: M, standard molecular weight Marker; Load, protein extract; FT, flow-through fraction; Wash: the impurity-washing fraction; Elu, elution fraction; Elu (10×), 10 times concentrated elution fraction.

1.3 Optimization of Cation Chromatographic Parameters Resin as Primary Purification Process 1.3.1 Optimization of Chromatographic Conditions Using BGL SP HP Resin In order to better connect the cation exchange chromatography, the Tris buffer system was used to the PB buffer system to follow the same extraction conditions. We found that the clarity of the crude extract were largely improved. The stability of the crude extract was studied by adjusting the pH. As shown in FIG. 14, we found when lower than pH6.5, the crude extract became turbid, therefore, the optimized loading buffer pH is 7.0 for chromatography using BGL SP HP resin. Finally, the optimized washing condition is optimized as the washing buffer comprising of 20 mM PB, 130 mM NaCl, pH 5.9; and the elution buffer comprising of 20 mM PB, 100 mM NaCl, pH 6.95. The results of the chromatography are shown in FIG. 15.

1.3.2 Optimization of Chromatographic Conditions Using NW Nano Gel 50 SP

Figure 16:
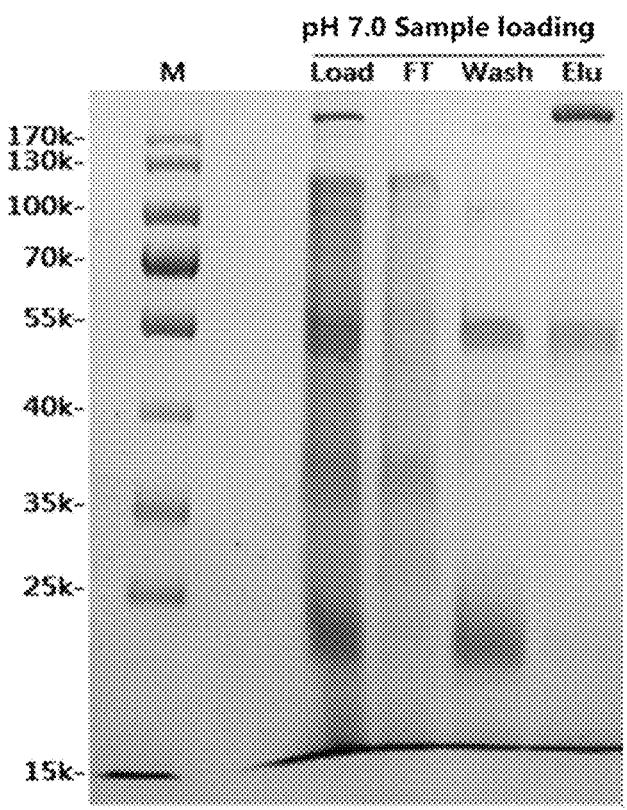
FIG. 16 shows the SDS-PAGE image of elution of OsrFN at NW Nano Gel 50 SP resin, where: M, standard molecular weight Marker; Load, protein extract; FT, flow-through fraction; Wash, impurity-washing fraction; Elu, elution fraction.

To compare alternative resin, NW Nano Gel 50 SP is used, which is a resin with highly cross-linked porous polystyrene microspheres. It has the characteristics of high flow rate, high load capacity, high salt resistance and low back pressure etc. The study found t that loading capacity of Nano Gel 50 SP reached up to 22.7 g rice powder/mL resin at high flow rates. After pilot test, a safe loading capacity is of 12.5 g rice powder/mL resin, which is more suitable for the capture step. The chromatography conditions are optimized as washing buffer comprising 20 mM PB, 150 mM NaCl, pH 7.0, the elution buffer comprising 20 mM PB, 300 mM NaCl, pH 7.0. The results of the chromatographic samples are shown in FIG. 16.

2. Optimization of Final Purification Processing of OsrhFn

Figure 17:
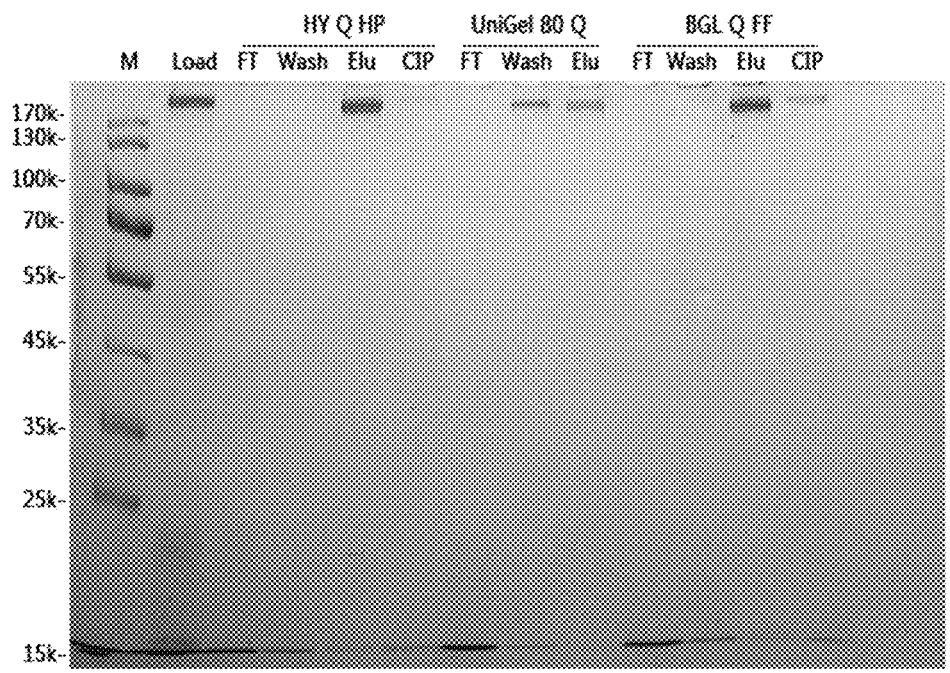
FIG. 17 shows the SDS-PAGE image of OsrFN purity at different chromatographic resins of HY Q HP, NW UniGel 80 Q, BGL Q FF filler, where: M, standard molecular weight Marker; Load, elution fraction collected from Nano Gel 50 SP chromatography; FT, flow-through fraction; Wash, impurity-washing fraction; Elu, elution fraction; CIP, regenerated solution.

In order to obtain a simple and optimized purification process for OsrFN, three resins, HY Q HP, BLG Q FF, and NW UniGel 80 Q were used for further study based on the preliminary research results. We found that HY Q HP and BLG Q FF presented high performance of separation effects. Under the same conditions, the salt concentration for eluting target protein on UniGel 80 Q was reduced, which was beneficial to the later process. Taken together, Q FF was a best resin for final purification, and Q HP as an alternative. The results are shown in FIG. 17.

Example 4: Two-Step Purification Process of BLG SP HP and HY Q HP

According to the results of the chromatographic conditions of primary purification and final purification in Example 3, the two-step chromatography comprising of BLG SP HP and HY Q HP was determined as one of final processes for the separation and purification of OsrhFn.

Figure 18:
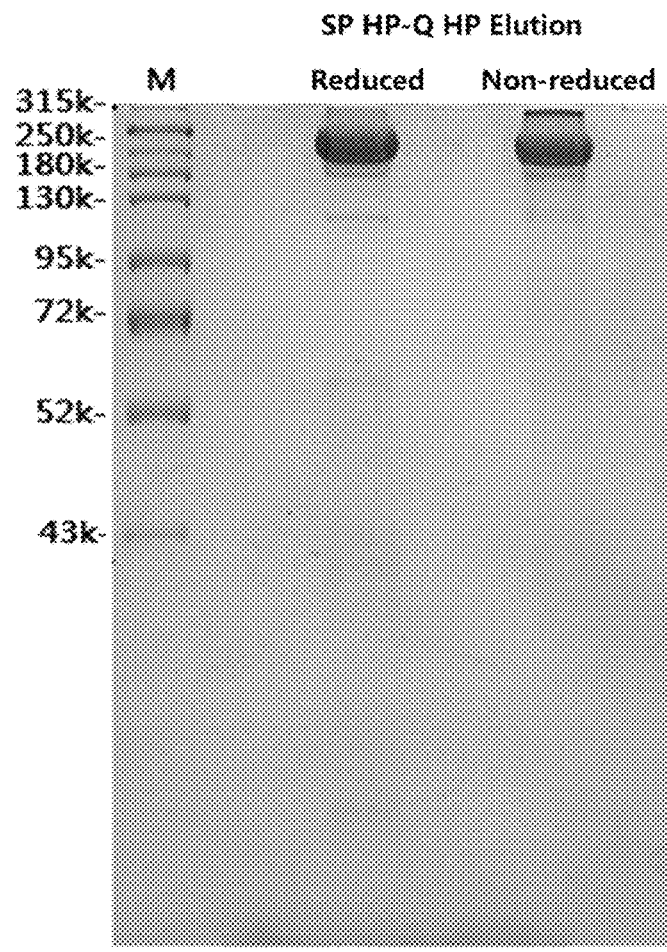
FIG. 18 shows the SDS-PAGE image for OsrFN purity of combined the two-step chromatography BLG SP HP and HY Q HP, where: M, standard molecular weight Marker; Reduced, samples of elution fraction for HY Q HP chromatography treated with a reducing loading buffer; Non-reduced, samples of elution fraction for HY Q HP chromatography treated with a non-reducing loading buffer.

1) Extraction: 1000 g of genetically engineered rice powder was extracted as described in Example 1.
2) First step of cation exchange chromatography as primary purification: Chromatography was performed on a chromatography column with 235 ml SP Bestarose HP using 20 mM PB, pH 7.0 as equilibration buffer, 20 mM PB, 130 mM NaCl, pH 5.9 as impurity-washing buffer and 20 mM PB, 100 mM NaCl, pH 7.0 as elution buffer.
3) Anion exchange chromatography as final purification: Chromatography was performed on a chromatography column with 28 ml HY Q HP, using 20 mM PB, pH 7.0 as equilibration buffer, 20 mM PB, 200 mM NaCl, pH 7.0 as impurity-washing buffer, 20 mM PB, 300 mM NaCl, pH 7.0 as elution buffer. The results of SDS-PAGE of products from different the chromatographic steps are shown in FIG. 18.

Example 5: Two-Step Purification Process of NY NanoGel 50 SP-BLG Q FF

According to the primary results of the chromatographic conditions in Example 3, the two-step chromatography comprising of NW NanoGel 50 SP-BLG Q FF was used as one of final processes for the separation and purification of OsrhFn.

Figure 19:
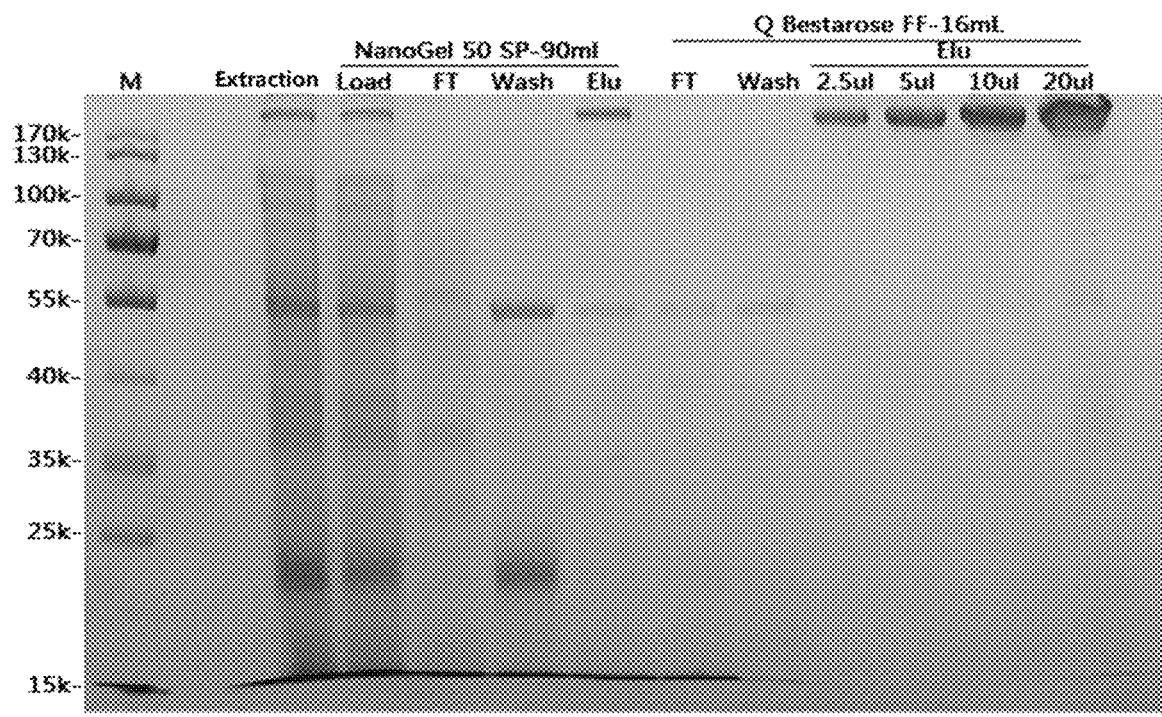
FIG. 19 shows the SDS-PAGE image for separation effects of two-step chromatography of NY Nano Gel 50 SP-BLG Q FF, where: M, standard molecular weight Marker; Load, sample of protein extract after pH adjustment for loading; FT: flow-through fraction; Wash: impurity-washing fraction, Elu: elution fraction.
Figure 20:
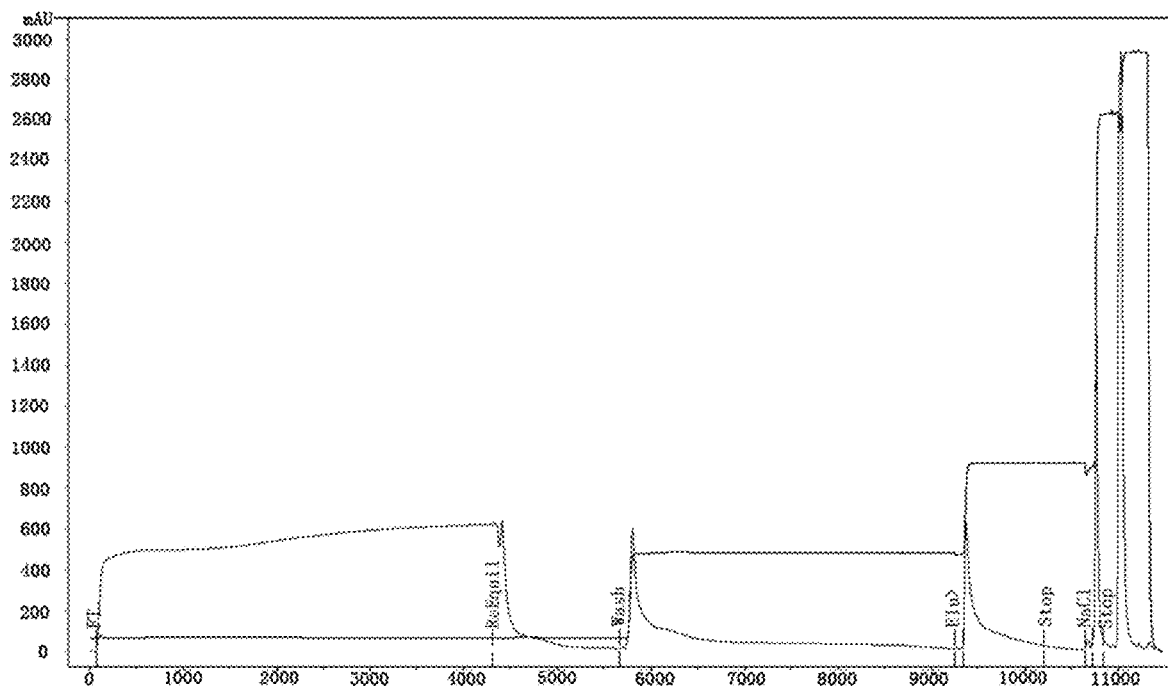
FIG. 20 is a chromatogram for NY Nano Gel 50 SP.
Figure 21:
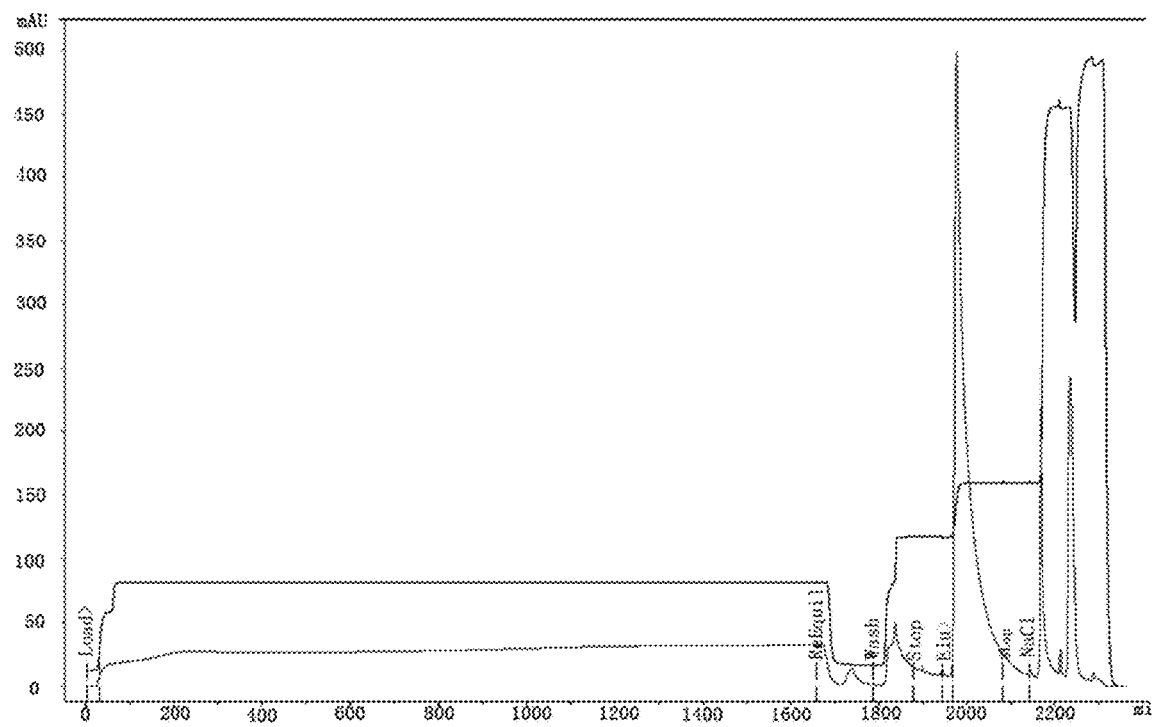
FIG. 21 is a chromatogram for BLG Q FF.
Figure 22:
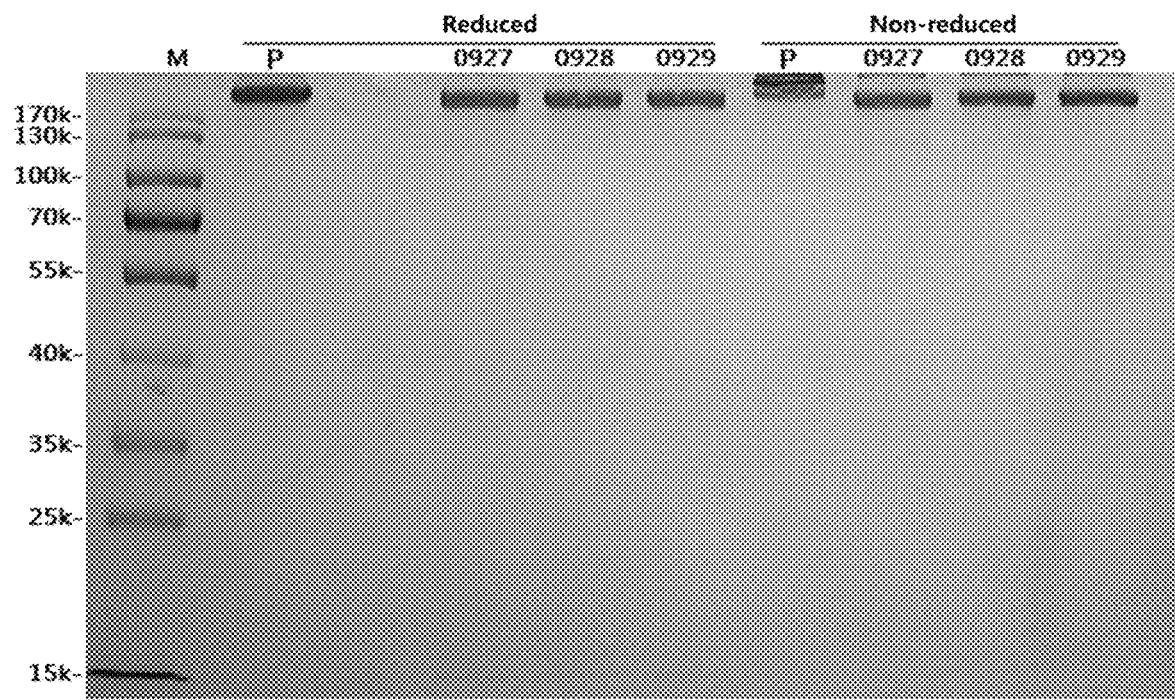
FIG. 22 shows the SDS-PAGE image of OsrFN purity using the two-step chromatographic process of NY Nano Gel 50 SP and BLG Q FF, where: M, standard molecular weight Marker; P, Fn positive reference; 0927, 0928, and 0929 are samples of different batches; Reducing: reducing electrophoresis; Non-reducing: non-reducing electrophoresis.
Figure 23:
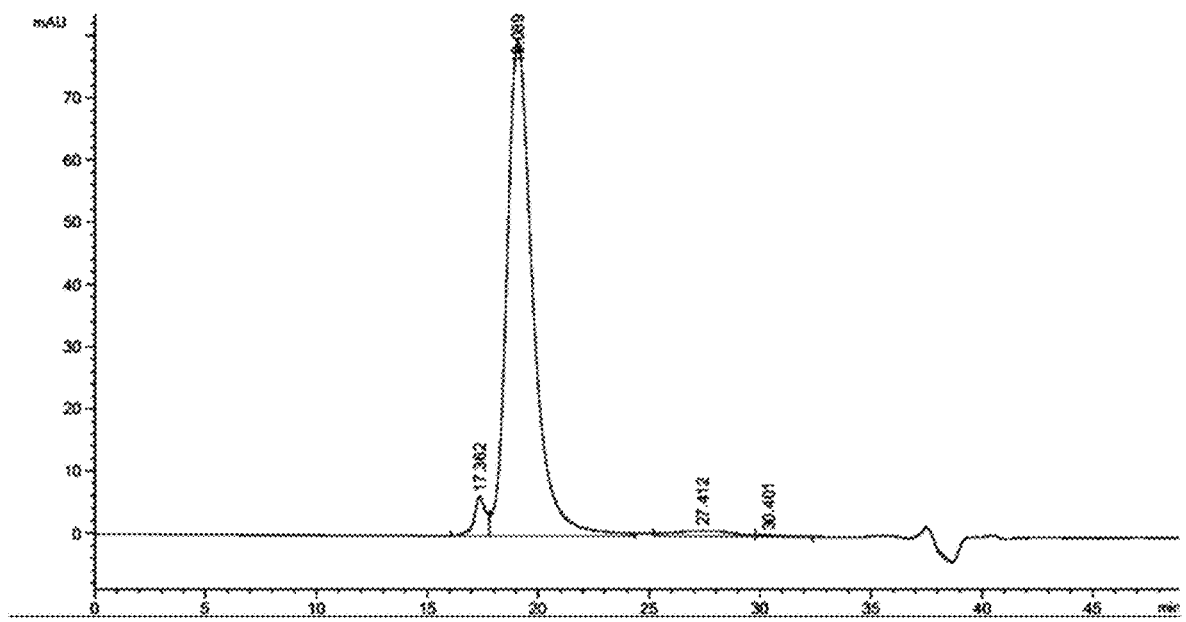
FIG. 23 shows the SEC-HPLC profile of the OsrFN of the two-step chromatography using NY Nano Gel 50 SP and BLG Q FF.
Figure 24:
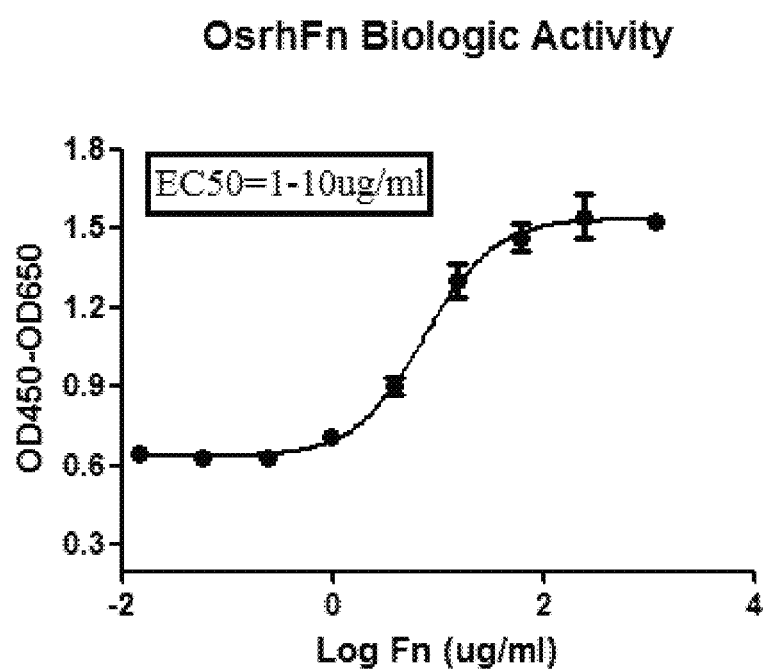
FIG. 24 shows the bioactivity assay of OsrFN obtained by the two-step chromatography of NY Nano Gel 50 SP and BLG Q FF.

1) Extraction: 1000 g of genetically engineered rice powder was extracted as described in Example 1.
2) Cation exchange chromatography as primary purification: Chromatography was performed using a chromatography column with 90 ml Nano Gel 50 SP using 20 mM PB, pH 7.0 as equilibration buffer, 20 mM PB, 140 mM NaCl, pH 7.0 as impurity-washing buffer and 20 mM PB, 300 mM NaCl, pH 7.0 as elution buffer.
3) Anion exchange chromatography as final purification: Chromatography was performed using a chromatography column with 16 ml BLG Q FF, using 20 mM PB, pH 7.0 as equilibration buffer, 20 mM PB, 200 mM NaCl, pH 7.0 as impurity-washing buffer and 20 mM PB, 300 mM NaCl, pH 7.0 as elution buffer. The results of SDS-PAGE of products from different the chromatographic steps are shown in FIG. 19

Example 6: Validation of Purification Process of OsrhFn

In order to validate the lab-scale manufacturing process, the optimized two-step chromatographic process comprising of NW Nano Gel 50 SP and BLG Q FF was performed for three times. The specific implementation steps of the validation procedure are as follows:

1) Extraction: 7.7 g of GSH (dissolved in 100 mL of ultrapure water) was added to 5000 mL of extraction buffer (20 mM PB, pH 8.0) and then 0.87 g of PMSF (dissolved in 435 mL of isopropanol and 5 ml of Tween 80 were added. After mixed well, 1 kg of rice powder containing Fn was added into the extraction solution and stirred at room temperature for 1 hour; and then 250 g of filter aid was added. Filtration using filtered under positive pressure is conducted. The filtrate was filtered with a 0.45 μm filter membrane to obtain a crude extract.
2), Cation exchange chromatography as primary purification: Chromatography was equilibrated using the equilibration buffer (20 mM PB, pH 7.0), impurity-washing buffer (20 mM PB, 140 mM NaCl, pH 7.0) and elution buffer (20 mM PB, 300 mM NaCl, pH 7.0) to operate the primary purification of OsrFn. The chromatogram is shown in FIG. 20.
3) Anion exchange chromatography as final purification: Chromatography was performed using equilibration buffer (20 mM PB, pH 7.0), impurity-washing buffer (20 mM PB, 200 mM NaCl, pH 7.0) and, elution buffer (20 mM PB, 300 mM NaCl, pH 7.0) to operate final purification of OsrFn. The chromatogram is shown in FIG. 21.

The results of the purity, the protein concentration and the yield of the three validation batches are summarized in the table below.

| Validation batch No. | Purity (%) | Concentration (mg/mL) | Volume (mL) | Yield (mg/kg rice powder) | Average yield (mg/kg rice powder) | RSD (%) |
|---|---|---|---|---|---|---|
| 20180927 | 97.1 | 0.754 | 124.7 | 94.0 | 85.8 | 8.2 |
| 20180928 | 96.0 | 0.726 | 112.6 | 81.7 | | |
| 20180929 | 95.4 | 0.732 | 111.6 | 81.7 | | |

The results of SDS-PAGE from three validation batches are shown in FIG. 22. The purity of the OsrFn is greater than 95%. As shown in FIG. 23, the SEC-HPLC profile of OsrFn from the two-step chromatographic purification process of NY Nano Gel 50 SP and BLG Q FF. The cell activity of OsrFn from the two-step chromatographic purification process showed in FIG. 24. Both the purity and the activity of OsrFn meet the positive control.

What is claimed is:

1. A chromatographic method for separating and purifying a recombinant human fibronectin protein from genetically engineered rice seeds or grains expressing the recombinant human fibronectin protein, comprising the following steps in sequence:
   1) extracting the recombinant human fibronectin protein from the genetically engineered rice seeds or grains comprising the recombinant human fibronectin protein to obtain a crude protein extract comprising the recombinant human fibronectin protein;
   2) subjecting a crude protein extract comprising the recombinant human fibronectin protein to cation exchange chromatography to obtain a primary product; and
   3) subjecting the primary product to anion exchange chromatography to obtain a purified recombinant human fibronectin protein,
   wherein the purified recombinant human fibronectin protein is prepared by a method comprising the steps of:
   (a) de-hulling and polishing the rice seeds or grain into a semi-polished rice using genetically engineered rice seeds or grains expressing recombinant human fibronectin protein;
   (b) grinding the semi-polished rice into a rice powder with a fineness of between 80-100 mesh;
   (c) providing a first buffer having a pH value of between 5.9-8.0 and comprising:
   between 10-50 mM Tris,
   between 10-50 mM sodium phosphate (PB),
   between 0-110 mM NaCl,
   between 0.8-1 mM phenylmethylsulfonyl fluoride (PMSF),
   between 5-10 mM glutathione (GSH),
   between 0.05-0.1% of a non-iconic surfactant, and
   an emulsifier comprising an ethoxylated sorbitan ester based oleic acid;
   (d) mixing the rice powder with the first buffer at a ratio of weight to volume of between 1:5-1:10 to generate a rice powder-comprising extraction buffer, and extracting the rice powder-comprising extraction buffer at room temperature (RT) for between 0.5-2 hours to obtain a crude protein extract comprising the human recombinant fibronectin protein;
   (e) equilibrating a cationic exchange resin using a cationic exchange equilibration buffer at a volume of between 5-15 times column volume at a flow rate of between 50-200 cm/h to generate an equilibrated cationic chromatography column,
   wherein the cationic exchange equilibration buffer has a pH value of between 6.8-7.1 and comprises between 10-50 mM sodium phosphate (PB) and between 0-120 mM NaCl;
   (f) loading the crude protein extract into the equilibrated cationic chromatography column, wherein the crude protein extract has a conductivity of between 2.5-13.5 ms/cm and a pH value of between 6.8-7.1;
   (g) removing protein impurities from the cationic chromatography column using a first impurity-washing buffer with between 20-40 times column volume at a flow rate of between 50-200 cm/h,
   wherein the first impurity-washing buffer has a pH value of between pH 6.8-7.1 and comprises between 10-50 mM PB and between 130-200 mM NaCl; and
   (h) eluting human recombinant fibronectin protein from the cationic chromatography column using a first elution buffer at a flow rate of between 50-200 cm/h to generate an elution fraction comprising the recombinant human fibronectin protein,
   wherein the first elution buffer has a pH value of between 6.8-7.1, and comprises between 10-50 mM PB and between 250-300 mM NaCl;
   (i) equilibrating an anion exchange chromatography column with an anion exchange equilibration buffer of 5-15 times column volume at a flow rate of between 50-200 cm/h,
   wherein the anion exchange equilibration buffer has a pH value of between 6.8-7.1, and comprises between 10-50 mM PB and between 0-150 mM NaCl;
   (j) loading the elution fraction comprising the recombinant human fibronectin protein onto the equilibrated anion exchange chromatography column;
   (k) eluting impurity proteins with a second impurity-washing buffer at a flow rate of 50-200 cm/h,
   wherein the second impurity-washing buffer has a pH value of between 6.8-7.1, and comprises between 10-50 mM PB and between 200-220 mM NaCl; and
   (l) eluting the human recombinant fibronectin protein with a second elution buffer at a flow rate of between 50-200 cm/h, to obtain an elution fraction comprising purified human recombinant fibronectin protein as a final product,
   wherein the second elution buffer has a pH value of between 6.8-7.1, and comprises between 10-50 mM PB and between 250-300 mM NaCl,
   thereby generating a purified human recombinant fibronectin protein.

2. The chromatographic method according to claim 1, wherein:
   the elution fraction comprising the recombinant human fibronectin protein of step (i) has a conductivity of between 12.5 to 17.6 ms/cm, and a pH value of between pH 6.8 to pH 7.1;
   the amount of phenylmethylsulfonyl fluoride (PMSF) in the first buffer is 1 mM;
   the amount of GSH in the first buffer is 5 mM;
   the amount of non-iconic surfactant in the first buffer is 0.1%;
   the cationic exchange equilibration buffer comprises 20 mM sodium phosphate (PB), pH 7.0,
   the first impurity-washing buffer comprises 20 mM sodium phosphate (PB), 145 mM NaCl, pH 7.0;
   the first elution buffer comprises 20 mM sodium phosphate (PB), 300 mM NaCl, pH 7.0;
   the anionic exchange equilibration buffer comprises 20 mM sodium phosphate (PB), pH 7.0;
   the second impurity-washing buffer comprises 20 mM sodium phosphate (PB), 200 mM NaCl, pH 7.0; and/or
   the second elution buffer comprises 20 mM sodium phosphate (PB), 300 mM NaCl, pH 7.0.

* * * * *